United States Patent
Masumoto et al.

(10) Patent No.: US 9,169,276 B2
(45) Date of Patent: Oct. 27, 2015

(54) ETHYNYLPHENYLAMIDINE COMPOUND OR SALT THEREOF, METHOD FOR PRODUCING SAME, AND FUNGICIDE FOR AGRICULTURAL AND HORTICULTURAL USE

(71) Applicant: OTSUKA AGRITECHNO CO., LTD., Tokyo (JP)

(72) Inventors: Satoru Masumoto, Tokushima (JP); Hitoshi Mutsutani, Naruto (JP); Sachi Kimura, Naruto (JP)

(73) Assignee: OTSUKA AGRITECHNO CO., LTD., Tokyo (JP)

(*) Notice: Subject to any disclaimer, the term of this patent is extended or adjusted under 35 U.S.C. 154(b) by 0 days.

(21) Appl. No.: 14/253,109

(22) Filed: Apr. 15, 2014

(65) Prior Publication Data

US 2014/0228588 A1 Aug. 14, 2014

Related U.S. Application Data

(62) Division of application No. 13/879,488, filed as application No. PCT/JP2011/075268 on Nov. 2, 2011, now Pat. No. 8,785,649.

(30) Foreign Application Priority Data

Nov. 5, 2010 (JP) .................... 2010-248118
Aug. 1, 2011 (JP) .................... 2011-168214

(51) Int. Cl.

| | |
|---|---|
| C07C 211/45 | (2006.01) |
| C07C 211/51 | (2006.01) |
| C07C 211/52 | (2006.01) |
| C07F 7/10 | (2006.01) |
| A01N 37/52 | (2006.01) |
| A01N 43/10 | (2006.01) |
| A01N 43/38 | (2006.01) |
| A01N 43/40 | (2006.01) |
| A01N 47/42 | (2006.01) |
| A01N 55/00 | (2006.01) |
| C07C 257/10 | (2006.01) |
| C07C 257/12 | (2006.01) |
| C07D 209/48 | (2006.01) |
| C07D 213/58 | (2006.01) |

(Continued)

(52) U.S. Cl.
CPC . *C07F 7/10* (2013.01); *A01N 33/00* (2013.01); *A01N 37/52* (2013.01); *A01N 43/10* (2013.01); *A01N 43/38* (2013.01); *A01N 43/40* (2013.01); *A01N 47/42* (2013.01); *A01N 55/00* (2013.01); *C07C 211/45* (2013.01); *C07C 211/52* (2013.01); *C07C 215/68* (2013.01); *C07C 257/10* (2013.01); *C07C 257/12* (2013.01); *C07C 275/12* (2013.01); *C07C 335/32* (2013.01); *C07D 209/48* (2013.01); *C07D 213/58* (2013.01); *C07D 333/20* (2013.01); *C07F 7/0818* (2013.01); *C07F 7/1852* (2013.01); *C07C 2101/14* (2013.01)

(58) Field of Classification Search
None
See application file for complete search history.

(56) References Cited

U.S. PATENT DOCUMENTS

| 6,100,429 A | 8/2000 | Gruber |
|---|---|---|
| 2006/0069261 A1 | 3/2006 | Bonneau et al. |

(Continued)

FOREIGN PATENT DOCUMENTS

| CN | 101565416 A | 10/2009 |
|---|---|---|
| JP | 56-123903 | 9/1981 |

(Continued)

OTHER PUBLICATIONS

Barrow et al, Tetrahedron (1976), 32(14), 1829-34.*

(Continued)

*Primary Examiner* — Zinna Northington Davis
(74) *Attorney, Agent, or Firm* — Kratz, Quintos & Hanson, LLP

(57) ABSTRACT

An object of the present invention is to provide a novel fungicide having an excellent fungicidal activity. The compound used as the fungicide of the present invention is an ethynylphenylamidine compound or a salt thereof, the compound being represented by Formula (1):

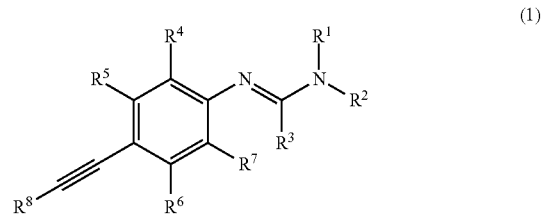

(1)

wherein $R^1$ and $R^2$ are each hydrogen or $C_{1-12}$ alkyl, or $R^1$ and $R^2$ may be bonded together to form $C_{1-7}$ alkylene;

$R^3$ is hydrogen or $C_{1-4}$ alkylthio;

$R^4$, $R^5$, $R^6$, and $R^7$ are each hydrogen, halogen, etc.; and $R^8$ is hydrogen, $C_{1-20}$ alkyl, $C_{3-8}$ cycloalkyl, $C_{1-4}$ haloalkyl, phenyl, a heterocyclic group, or —$(CH_2)n$-$Si(R^9)(R^{10})(R^{11})$ wherein $R^9$, $R^{10}$, and $R^{11}$ are each $C_{1-6}$ alkyl, and n is an integer of 0 or 1.

15 Claims, No Drawings

(51) Int. Cl.
  *C07D 333/20* (2006.01)
  *C07F 7/08* (2006.01)
  *A01N 33/00* (2006.01)
  *C07C 215/68* (2006.01)
  *C07C 275/12* (2006.01)
  *C07C 335/32* (2006.01)
  *C07F 7/18* (2006.01)

(56) References Cited

U.S. PATENT DOCUMENTS

| | | |
|---|---|---|
| 2006/0128747 A1 | 6/2006 | Burli |
| 2008/0287705 A1 | 11/2008 | Urazoe |
| 2010/0093533 A1 | 4/2010 | Kunz |
| 2010/0105552 A1 | 4/2010 | Kunz |
| 2010/0113276 A1 | 5/2010 | Kuhn |
| 2010/0120615 A1 | 5/2010 | Kunz |
| 2010/0167926 A1 | 7/2010 | Kunz |
| 2010/0304966 A1 | 12/2010 | Rheinheimer |
| 2012/0122678 A1 | 5/2012 | Kunz |
| 2013/0012742 A1 | 1/2013 | Kunz |

FOREIGN PATENT DOCUMENTS

| | | |
|---|---|---|
| JP | 2001-513529 A1 | 9/2001 |
| JP | 2002-536354 A1 | 10/2002 |
| JP | 2005-524706 A1 | 8/2005 |
| JP | 2010-502617 A1 | 1/2010 |
| JP | 2010-520898 A1 | 6/2010 |
| WO | 92/07831 | 5/1992 |
| WO | 92/07832 | 5/1992 |
| WO | WO 99/07674 A2 | 1/1999 |
| WO | WO 00/46184 A1 | 8/2000 |
| WO | 02/46166 | 6/2002 |
| WO | WO 03/093224 A1 | 11/2003 |
| WO | 2005/108405 A2 | 11/2005 |
| WO | 2005/108405 A3 | 11/2005 |
| WO | WO 2007/031508 A1 | 3/2007 |
| WO | WO 2007/031512 A2 | 3/2007 |
| WO | WO 2007/031526 A1 | 3/2007 |
| WO | WO 2007/061966 A2 | 5/2007 |
| WO | WO 2007/093227 A1 | 8/2007 |
| WO | WO 2008/027466 A1 | 3/2008 |
| WO | WO 2008/110280 A2 | 9/2008 |
| WO | WO 2008/110281 A2 | 9/2008 |
| WO | WO 2008/110313 A1 | 9/2008 |
| WO | WO 2008/110315 A1 | 9/2008 |
| WO | 2009/003589 A1 | 1/2009 |
| WO | WO 2009/053250 A1 | 4/2009 |
| WO | 2011/073172 A1 | 6/2011 |

OTHER PUBLICATIONS

Rosenberg et al, Tetrahedron (1971), 27(16), 3893-907.*
Claisse et al, Journal of the Chemical Society, Perkin Transactions 1: Organic and Bio-Organic Chemistry (1972-1999) (1973), (20), 2241-9.*
Safe, Organic Mass Spectrometry (1973), 7(12), 1329-36.*
Wei et al, Journal of the American Chemical Society (2001), 123(17), 4083-4084.*
Jeong et al, Journal of Organic Chemistry (1999), 64(26), 9459-9466.*
Catanescu et al, Liquid Crystals (2004), 31(4), 541-555.*
Tomizaki et al, Tetrahedron (2003), 59(8), 1191-1207.*
Lim et al, Journal of Materials Chemistry (2007), 17(19), 1969-1980.*
Mongin, Olivier, et al., "Synthesis of Nanometer-sized Homo- and Heteroorganometallic Tripaphyris," Tetrahedron, vol. 53, No. 20 (1997), pp. 6835-6846.
Erdelyl, Mate, et al. "Rapid Homogeneous-Phase Sonogashira Coupling Reactions Using Controlled Microwave Heating," J. Org. Chem., vol. 66, No. 12 (2001), pp. 4165-4169.
Ahmed, Mohamed S. Mohamed, et al., "Sonogashira Coupling with Aqueous Ammonia Directed to the Synthesis of Azotolane Derivatives," Tetrahedron, vol. 60 (2004), pp. 9977-9982.
Zhao, Dongbing, et al., "Copper-catalyzed Decarboxylative Cross-coupling of Alkynyl Carboxylic Acids with Aryl Halides," Chem. Commun., vol. 46 (2010), pp. 9049-9051.
Extended European Search Report dated May 15, 2014, in the corresponding European patent application No. 11838051.8.
R. Chinchilla, et al.; "The Sonogashira Reaction: A Booming Methodology in Synthetic Organic Chemistry;" Chemical Reviews; vol. 107; Feb. 17, 2007; pp. 874-922 (49 Sheets)/Cited in International Search Report.
International Search Report for International Application No. PCT/JP2011/075268 dated Dec. 6, 2011.

* cited by examiner

ETHYNYLPHENYLAMIDINE COMPOUND OR SALT THEREOF, METHOD FOR PRODUCING SAME, AND FUNGICIDE FOR AGRICULTURAL AND HORTICULTURAL USE

TECHNICAL FIELD

The present invention relates to an ethynylphenylamidine compound or a salt thereof, a method for producing the same, and an agricultural and horticultural fungicide.

BACKGROUND ART

Various compounds with a fungicidal activity for agricultural and horticultural use are known as compounds having an amidino group on the phenyl ring. Many of these compounds have a substituent in the para position of the amidino group, and the substituent is bonded via a heteroatom (oxygen, sulfur, or nitrogen) (see Patent Documents 1 to 10). However, the fungicidal activity of these compounds is insufficient.

There is also reported a compound having a substituent in the above-mentioned para-position directly bonded to a carbon atom without a heteroatom (see Patent Document 11). However, the compound of Patent Document 11 shows an excellent fungicidal activity when used at a high concentration, but has an insufficient effect in practical use as an agricultural and horticultural agent (see Comparative Test 1, described later).

Generally, long-term use of fungicides has recently led to the emergence of drug-resistant fungi. Accordingly, control by conventional fungicides, such as benzimidazole agents, has become difficult. There is thus an urgent demand for the development of a new type of drug that has a fungicidal activity not only on drug-sensitive fungi, but also on drug-resistant fungi.

CITATION LIST

Patent Literature

PTL 1: WO 2003/093224
PTL 2: WO 2007/031508
PTL 3: WO 2007/031526
PTL 4: WO 2007/061966
PTL 5: WO 2007/093227
PTL 6: WO 2008/110280
PTL 7: WO 2008/110281
PTL 8: WO 2008/110313
PTL 9: WO 2008/110315
PTL 10: WO 2009/053250
PTL 11: WO 2007/031512

SUMMARY OF INVENTION

Technical Problem

An object of the present invention is to provide a novel fungicide that has an excellent fungicidal activity not only on drug-sensitive fungi, but also on drug-resistant fungi.

Solution to Problem

As a result of extensive research to achieve the above object, the present inventors focused on the type of the substituent on the para-position of the phenyl ring substituted with an amidino group, and found that compounds substituted with an ethynyl group without a heteroatom exert a desired excellent fungicidal activity. The present invention has been completed based on this finding.

The present invention provides an ethynylphenylamidine compound or a salt thereof, a method for producing the same, and an agricultural and horticultural fungicide, as shown in the following Items 1 to 28.

Item 1. An ethynylphenylamidine compound or a salt thereof, the compound being represented by Formula (1):

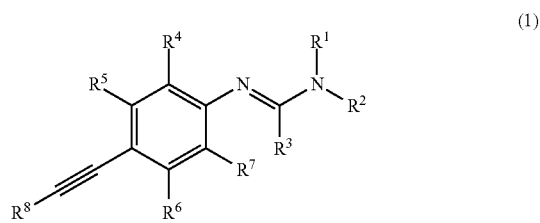

wherein $R^1$ and $R^2$ are each hydrogen or $C_{1-12}$ alkyl, or $R^1$ and $R^2$ may be bonded together to form $C_{1-7}$ alkylene;

$R^3$ is hydrogen or $C_{1-4}$ alkylthio;

$R^4$, $R^5$, $R^6$, and $R^7$ are each hydrogen, halogen, $C_{1-4}$ alkyl, $C_{1-4}$ haloalkyl, or $C_{1-4}$ haloalkoxy; and $R^8$ is hydrogen; $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or $-(CH_2)n-Si(R^9)(R^{10})(R^{11})$ wherein $R^9$, $R^{10}$, and $R^{11}$ are each $C_{1-6}$ alkyl, and n is an integer of 0 or 1.

Item 2. The ethynylphenylamidine compound or a salt thereof according to item 1, wherein the ethynylphenylamidine compound is represented by Formula (1) wherein $R^3$ is hydrogen.

Item 3. The ethynylphenylamidine compound or a salt thereof according to item 1 or 2, wherein the ethynylphenylamidine compound is represented by Formula (1) wherein $R^1$ and $R^2$ are each $C_{1-12}$ alkyl.

Item 4. The ethynylphenylamidine compound or a salt thereof according to any one of items 1 to 3, wherein the ethynylphenylamidine compound is represented by Formula (1) wherein $R^4$ or $R^7$ is halogen or $C_{1-4}$ alkyl.

Item 5. The ethynylphenylamidine compound according to any one of items 1 to 4, wherein the ethynylphenylamidine compound is represented by Formula (1) wherein $R^8$ is hydrogen; $C_{1-12}$ alkyl optionally substituted on the alkyl group with one or more substituents independently selected from the group consisting of $C_{1-4}$ alkoxy, hydroxy, cyano, and phenyl; $C_{3-8}$ cycloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group; or $-(CH_2)n-Si(R^9)(R^{10})(R^{11})$ wherein $R^9$, $R^{10}R^{11}$, and n are as defined in item 1.

Item 6. A method for producing an ethynylphenylamidine compound or a salt thereof, the compound being represented by Formula (1):

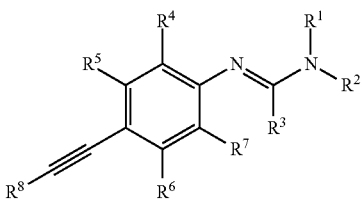

wherein $R^1$ and $R^2$ are each hydrogen or $C_{1-12}$ alkyl, or $R^1$ and $R^2$ may be bonded together to form $C_{1-7}$ alkylene;

$R^3$ is hydrogen or $C_{1-4}$ alkylthio;

$R^4$, $R^5$, $R^6$, and $R^7$ are each hydrogen, halogen, $C_{1-4}$ alkyl, $C_{1-4}$ haloalkyl, or $C_{1-4}$ haloalkoxy; and $R^8$ is hydrogen; $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —$(CH_2)n$-$Si(R^9)(R^{10})(R^{11})$ wherein $R^9$, $R^{10}$, and $R^{11}$ are each $C_{1-6}$ alkyl, and n is an integer of 0 or 1;

the method comprising:

reacting a phenylamidine compound represented by Formula (2):

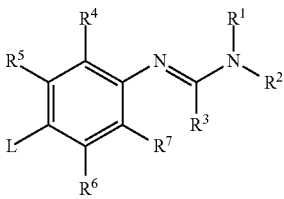

wherein $R^1$, $R^2$, $R^3$, $R^4$, $R^5$, $R^6$, and $R^7$ are as defined above, and L is a leaving group, with an acetylene compound represented by Formula (3):

$R^8$-≡  (3)

wherein $R^8$ is as defined above, in the presence of a palladium catalyst and a base.

Item 7. A method for producing an ethynylphenylamidine compound or a salt thereof, the compound being represented by Formula (1):

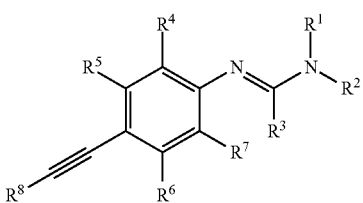

wherein $R^1$ and $R^2$ are each hydrogen or $C_{1-12}$ alkyl, or $R^1$ and $R^2$ may be bonded together to form $C_{1-7}$ alkylene;

$R^3$ is hydrogen or $C_{1-4}$ alkylthio;

$R^4$, $R^5$, $R^6$, and $R^7$ are each hydrogen, halogen, $C_{1-4}$ alkyl, $C_{1-4}$ haloalkyl, or $C_{1-4}$ haloalkoxy; and $R^8$ is hydrogen; $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —$(CH_2)n$-$Si(R^9)(R^{10})(R^{11})$ wherein $R^9$, $R^{10}$, and $R^{11}$ are each $C_{1-6}$ alkyl, and n is an integer of 0 or 1;

the method comprising:

reacting an ethynylaniline compound represented by Formula (4):

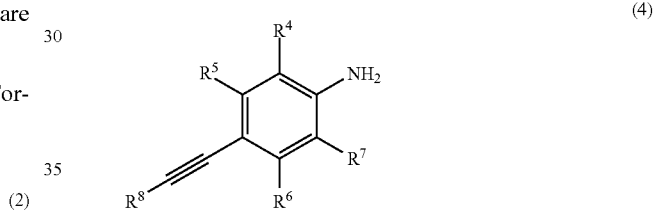

wherein $R^4$, $R^5$, $R^6$, $R^7$, and $R^8$ are as defined above, with an ortho-ester compound represented by Formula (5):

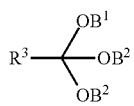

wherein $R^3$ is as defined above, and $B^1$ and $B^2$ are each $C_{1-4}$ alkyl or $C_{3-8}$ cycloalkyl, in the presence of an acid; and reacting the produced compound with an amine compound represented by Formula (6):

wherein $R^1$ and $R^2$ are as defined above.

Item 8. A method for producing an ethynylphenylamidine compound or a salt thereof, the compound being represented by Formula (1):

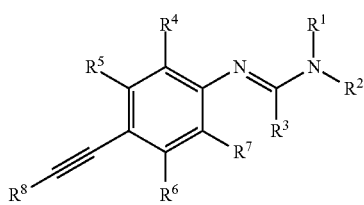

(1)

wherein $R^1$ and $R^2$ are each hydrogen or $C_{1-12}$ alkyl, or $R^1$ and $R^2$ may be bonded together to form $C_{1-7}$ alkylene;

$R^3$ is hydrogen or $C_{1-4}$ alkylthio;

$R^4$, $R^5$, $R^6$, and $R^7$ are each hydrogen, halogen, $C_{1-4}$ alkyl, $C_{1-4}$ haloalkyl, or $C_{1-4}$ haloalkoxy; and $R^8$ is hydrogen; $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —(CH$_2$)n-Si($R^9$)($R^{10}$)($R^{11}$) wherein $R^9$, $R^{10}$, and $R^{11}$ are each $C_{1-6}$ alkyl, and n is an integer of 0 or 1;

the method comprising:

reacting an ethynylaniline compound represented by Formula (4):

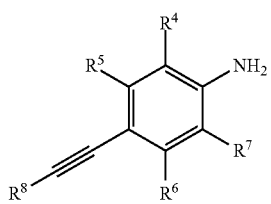

(4)

wherein $R^4$, $R^5$, $R^6$, $R^7$, and $R^8$ are as defined above, with an amide compound represented by Formula (7):

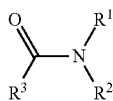

(7)

wherein $R^1$, $R^2$, and $R^3$ are as defined above, in the presence of a halogenating agent.

Item 9. A method for producing an ethynylphenylamidine compound or a salt thereof, the compound being represented by Formula (1):

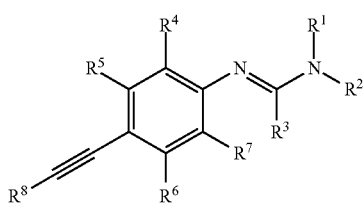

(1)

wherein $R^1$ and $R^2$ are each hydrogen or $C_{1-12}$ alkyl, or $R^1$ and $R^2$ may be bonded together to form $C_{1-7}$ alkylene;

$R^3$ is hydrogen or $C_{1-4}$ alkylthio;

$R^4$, $R^5$, $R^6$, and $R^7$ are each hydrogen, halogen, $C_{1-4}$ alkyl, $C_{1-4}$ haloalkyl, or $C_{1-4}$ haloalkoxy;

$R^8$ is hydrogen; $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —(CH$_2$)n-Si($R^9$)($R^{10}$)($R^{11}$) wherein $R^9$, $R^{10}$, and $R^{11}$ are each $C_{1-6}$ alkyl, and n is an integer of 0 or 1;

the method comprising:

reacting an ethynylaniline compound represented by Formula (4):

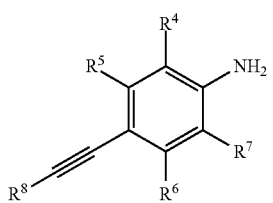

(4)

wherein $R^4$, $R^5$, $R^6$, $R^7$, and $R^8$ are as defined above, with an aminoacetal compound represented by Formula (8):

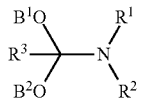

(8)

wherein $R^1$, $R^2$, $R^3$, $B^1$, and $B^2$ are as defined above, in the presence of an acid.

Item 10. An agricultural and horticultural fungicide comprising the ethynylphenylamidine compound or a salt thereof according to any one of items 1 to 4 as an active ingredient.

Item 11. An ethynylaniline compound represented by Formula (4):

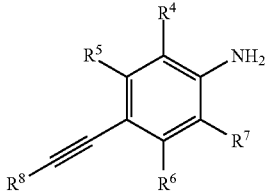

(4)

wherein $R^4$, $R^5$, $R^6$, and $R^7$ are each hydrogen, halogen, $C_{1-4}$ alkyl, $C_{1-4}$ haloalkyl, or $C_{1-4}$ haloalkoxy; and $R^8$ is hydrogen; $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —$(CH_2)n$-$Si(R^9)(R^{10})(R^{11})$ wherein $R^9$, $R^{10}$, and $R^{11}$ are each $C_{1-6}$ alkyl, and n is an integer of 0 or 1.

Item 12. The ethynylphenylamidine compound or a salt thereof according to item 3, wherein the ethynylphenylamidine compound is represented by Formula (1) wherein $R^1$ and $R^2$ are each $C_{1-4}$ alkyl.

Item 13. The ethynylphenylamidine compound or a salt thereof according to item 11, wherein the ethynylphenylamidine compound is represented by Formula (1) wherein $R^1$ and $R^2$ are each methyl or ethyl.

Item 14. The ethynylphenylamidine compound or a salt thereof according to item 4, wherein the ethynylphenylamidine compound is represented by Formula (1) wherein $R^4$ or $R^7$ is fluorine, chlorine, or methyl.

Item 15. The ethynylphenylamidine compound or a salt thereof according to item 13, wherein the ethynylphenylamidine compound is represented by Formula (1) wherein $R^4$ or $R^7$ is methyl.

Item 16. The ethynylphenylamidine compound or a salt thereof according to item 1 or 2, wherein the ethynylphenylamidine compound is represented by Formula (1) wherein $R^5$ and $R^7$ are each hydrogen, and $R^4$ and $R^6$ are each halogen or $C_{1-4}$ alkyl.

Item 17. The ethynylphenylamidine compound or a salt thereof according to item 15, wherein the ethynylphenylamidine compound is represented by Formula (1) wherein $R^5$ and $R^7$ are each hydrogen, and $R^4$ and $R^6$ are each fluorine, chlorine, or methyl.

Item 18. The ethynylphenylamidine compound or a salt thereof according to item 15, wherein the ethynylphenylamidine compound is represented by Formula (1) wherein $R^5$ and $R^7$ are each hydrogen, and $R^4$ and $R^6$ are each methyl.

Item 19. The ethynylphenylamidine compound according to item 5, wherein the ethynylphenylamidine compound is represented by Formula (1) wherein $R^8$ is $C_{1-12}$ alkyl optionally substituted on the alkyl group with one or more substituents independently selected from the group consisting of hydroxy, cyano, and phenyl; phenyl optionally substituted on the phenyl ring with one to five substituents selected from the group consisting of halogen, $C_{1-6}$ alkyl, and $C_{1-4}$ haloalkyl; or —$(CH_2)n$-$Si(R^9)(R^{10})(R^{11})$ wherein $R^9$, $R^{10}$, $R^{11}$, and n are as defined in item 1.

Item 20. The ethynylphenylamidine compound according to item 18, wherein the ethynylphenylamidine compound is represented by Formula (1) wherein $R^8$ is $C_{1-6}$ alkyl, phenyl, or —$(CH_2)n$-$Si(R^9)(R^{10})(R^{11})$ wherein $R^9$, $R^{10}$, $R^{11}$, and n are as defined in item 1.

Item 21. The ethynylphenylamidine compound according to item 20, wherein the ethynylphenylamidine compound is represented by Formula (1) wherein $R^8$ is $C_{1-6}$ alkyl.

Item 22. The ethynylphenylamidine compound according to item 20, wherein the ethynylphenylamidine compound is represented by Formula (1) wherein $R^8$ is phenyl.

Item 23. The ethynylphenylamidine compound according to item 20, wherein the ethynylphenylamidine compound is represented by Formula (1) wherein $R^8$ is —$(CH_2)n$-$Si(R^9)(R^{10})(R^{11})$ wherein $R^9$, $R^{10}$, and $R^{11}$ are as defined in item 1, and n is 0.

Item 24. The ethynylphenylamidine compound according to item 20, wherein the ethynylphenylamidine compound is represented by Formula (1) wherein $R^8$ is —$(CH_2)n$-$Si(R^9)(R^{10})(R^{11})$ wherein $R^9$, $R^{10}$, and $R^{11}$ are as defined in item 1, and n is 1.

Item 25. The ethynylphenylamidine compound according to item 18, wherein the ethynylphenylamidine compound is represented by Formula (1) wherein $R^8$ is tert-butyl, phenyl, trimethylsilyl, triethylsilyl, triisopropylsilyl, tert-butyldimethylsilyl, or trimethylsilylmethyl.

Item 26. A method for producing an ethynylphenylamidine compound represented by Formula (1) or a salt thereof, the method comprising reacting a phenylamidine compound represented by Formula (2) with an acetylene compound represented by Formula (3) in the presence of a palladium catalyst, a copper catalyst, and a base.

Item 27. The ethynylaniline compound according to item 11, wherein the ethynylaniline compound is represented by Formula (4) wherein $R^4$, $R^5$, $R^6$, and $R^7$ are each hydrogen, halogen, or $C_{1-4}$ alkyl; and $R^8$ is hydrogen; $C_{1-6}$ alkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; or —$(CH_2)n$-$Si(R^9)(R^{10})(R^{11})$ wherein $R^9$, $R^{10}$, $R^{11}$, and n are as defined in item 1.

Item 28. The ethynylaniline compound according to item 11 or 27, wherein the ethynylaniline compound is represented by Formula (4) wherein $R^8$ is tert-butyl, phenyl, trimethylsilyl, triethylsilyl, triisopropylsilyl, trimethylsilylmethyl, or tert-butyldimethylsilyl.

Each of the groups shown in the specification is described below.

Examples of the $C_{1-4}$ alkyl group include linear or branched alkyl groups having 1 to 4 carbon atoms, such as methyl, ethyl, n-propyl, isopropyl, n-butyl, isobutyl, sec-butyl, and tert-butyl.

Examples of the $C_{1-6}$ alkyl group include linear or branched alkyl groups having 1 to 6 carbon atoms, such as n-pentyl, isopentyl, neopentyl, tert-pentyl, n-hexyl, and isohexyl, in addition to those mentioned as examples of the $C_{1-4}$ alkyl group.

Examples of the $C_{1-12}$ alkyl group include linear or branched alkyl groups having 1 to 12 carbon atoms, such as n-heptyl, isoheptyl, n-octyl, isooctyl, n-nonyl, isononyl, n-decyl, isodecyl, n-undecyl, isoundecyl, n-dodecyl, and isododecyl, in addition to those mentioned as examples of the $C_{1-6}$ alkyl group.

Examples of the $C_{1-20}$ alkyl group include linear or branched alkyl groups having 1 to 20 carbon atoms, such as n-tridecyl, n-tetradecyl, n-pentadecyl, n-hexadecyl, n-heptadecyl, n-octadecyl, n-nonadecyl, and n-icosanyl, in addition to those mentioned as examples of the $C_{1-12}$ alkyl group.

These alkyl groups may be substituted at any substitutable position with 1 to 5 (preferably 1 to 3) substituents selected from, for example, $C_{1-4}$ alkoxy, cyano, phenyl, phenoxy, and optionally substituted heterocyclic groups.

Examples of the $C_{1-4}$ alkoxy group include linear or branched alkoxy groups having 1 to 4 carbon atoms, such as methoxy, ethoxy, n-propoxy, isopropoxy, cyclopropyloxy, n-butoxy, sec-butoxy, and tert-butoxy.

Examples of the $C_{1-4}$ alkylthio group include linear or branched alkylthio groups having 1 to 4 carbon atoms, such as methylthio, ethylthio, n-propylthio, isopropylthio, and tert-butylthio.

Examples of the $C_{1-4}$ haloalkyl group include linear or branched alkyl groups having 1 to 4 carbon atoms and substituted with 1 to 9, preferably 1 to 5, halogen atoms. Specific examples thereof include fluoromethyl, chloromethyl, bromomethyl, iodomethyl, difluoromethyl, trifluoromethyl, chlorodifluoromethyl, bromodifluoromethyl, dichlorofluoromethyl, 1-fluoroethyl, 2-fluoroethyl, 2-chloroethyl, 2-bromoethyl, 2-iodoethyl, 2,2,2-trifluoroethyl, 2,2,2-trichloroethyl, pentafluoroethyl, 1-fluoroisopropyl, 3-fluoropropyl, 3-chloropropyl, 3-bromopropyl, heptafluoropropyl, 4-fluorobutyl, 4-chlorobutyl, nonafluorobutyl, and like groups.

Examples of the $C_{1-4}$ haloalkoxy group include linear or branched alkoxy groups having 1 to 4 carbon atoms and substituted with 1 to 9, preferably 1 to 5, halogen atoms. Specific examples thereof include fluoromethoxy, chloromethoxy, bromomethoxy, iodomethoxy, dichloromethoxy, trichloromethoxy, difluoromethoxy, trifluoromethoxy, chlorodifluoromethoxy, bromodifluoromethoxy, dichlorofluoromethoxy, 1-fluoroethoxy, 2-fluoroethoxy, 2-chloroethoxy, 2-bromoethoxy, 2-iodoethoxy, 2,2,2-trifluoroethoxy, 2,2,2-trichloroethoxy, pentafluoroethoxy, 1-fluoroisopropoxy, 3-fluoropropoxy, 3-chloropropoxy, 3-bromopropoxy, 4-fluorobutoxy, 4-chlorobutoxy, and like groups.

Examples of the heterocyclic group include thienyl, furyl, tetrahydrofuryl, dioxolanyl, dioxanyl, pyrrolyl, pyrrolinyl, pyrrolidinyl, oxazolyl, isoxazolyl, oxazolinyl, oxazolidinyl, isoxazolinyl, triazolyl, isothiazolyl, triazolinyl, thiazolidinyl, isothiazolinyl, pyrazolyl, pyrazolidinyl, imidazolyl, imidazolinyl, imidazolidinyl, oxadiazolyl, oxadiazolinyl, thiadiazolinyl, triazolyl, triazolinyl, triazolidinyl, tetrazolyl, tetrazolinyl, pyridyl, dihydropyridyl, tetrahydropyridyl, piperidyl, oxazinyl, dihydrooxazinyl, morpholino, triazinyl, dihydrothiazinyl, thiamorpholino, pyridazinyl, dihydropyridazinyl, tetrahydropyridazinyl, hexahydropyridazinyl, oxadiazinyl, dihydrooxadiazinyl, tetrahydrooxadiazinyl, thiadiazolyl, thiadiazinyl, dihydrothiadiazinyl, tetrahydrothiadiazinyl, pyrimidinyl, dihydropyrimidinyl, tetrahydropyrimidinyl, hexahydropyrimidinyl, pyrazinyl, dihydropyrazinyl, tetrahydropyrazinyl, piperazinyl, triazinyl, dihydrotriazinyl, tetrahydrotriazinyl, hexahydrotriazinyl, tetrazinyl, dihydrotetrazinyl, indolyl, indolinyl, isoindolyl, indazolyl, quinazolinyl, dihydroquinazolyl, tetrahydroquinazolyl, carbazolyl, benzoxazolyl, benzoxazolinyl, benzisoxazolyl, benzisoxazolinyl, benzothiazolyl, benzisothiazolyl, benzisothiazolinyl, benzimidazolyl, indazolinyl, quinolinyl, dihydroquinolinyl, tetrahydroquinolinyl, isoquinolinyl, dihydroisoquinolinyl, tetrahydroisoquinolinyl, pyridoindolyl, dihydrobenzoxazinyl, cinnolinyl, dihydrocinnolinyl, tetrahydrocinnolinyl, phthalazinyl, dihydrophthalazinyl, tetrahydrophthalazinyl, quinoxalinyl, dihydroquinoxalinyl, tetrahydroquinoxalinyl, purinyl, dihydrobenzotriazinyl, dihydrobenzotetrazinyl, phenothiazinylfuranyl, benzofuranyl, benzothienyl, and like groups.

These heterocyclic groups include those substituted at any substitutable position with an oxo or thioketone group. These heterocyclic groups further include those optionally substituted at any substitutable position with 1 to 5 (preferably 1 to 3) substituents selected from, for example, halogen, $C_{1-4}$ alkyl, $C_{1-4}$ haloalkyl, and substituted heterocyclic groups (e.g., 3-chloropyridin-2-yl, 4-trifluoromethyl-1,3-thiazol-2-yl, and 5-trifluoromethylpyridin-2-yl).

Among these heterocyclic rings, thienyl, furyl, tetrahydrofuryl, dioxolanyl, dioxanyl, oxazolyl, isoxazolyl, thiazolyl, pyrazolyl, pyridyl, piperidyl, and phthalimide are preferable; and thienyl, tetrahydrofuryl, dioxolanyl, dioxanyl, thiazolyl, pyridyl, and phthalimide are particularly preferable.

Examples of the $C_{3-8}$ cycloalkyl group include cyclic alkyl groups having 3 to 8 carbon atoms, such as cyclopropyl, cyclobutyl, cyclopentyl, cyclohexyl, cycloheptyl, and cyclooctyl.

Examples of the alkylene group include methylene, ethylene, trimethylene, tetramethylene, pentamethylene, hexamethylene, and heptamethylene. These alkylene groups may contain optionally substituted nitrogen, oxygen, sulfur, or other atoms. Examples of such alkylene groups include —CH$_2$NHCH$_2$—, —CH$_2$NHCH$_2$CH$_2$—, —CH$_2$NHNHCH$_2$—, —CH$_2$CH$_2$NHCH$_2$CH$_2$—, —CH$_2$NHNHCH$_2$CH$_2$—, —CH$_2$NHCH$_2$NHCH$_2$—, —CH$_2$CH$_2$CH$_2$NHCH$_2$CH$_2$CH$_2$—, —CH$_2$OCH$_2$CH$_2$—, —CH$_2$CH$_2$OCH$_2$CH$_2$—, —CH$_2$SCH$_2$CH$_2$—, —CH$_2$CH$_2$SCH$_2$CH$_2$—, and like groups. These alkylene groups may be substituted at any position or on the nitrogen atom with one or more substituents selected from, for example, $C_{1-4}$ alkyl, $C_{1-6}$ alkoxycarbonyl, and hydroxy.

Examples of the leaving group include halogen atoms, such as fluorine, chlorine, bromine, and iodine; sulfonyloxy groups, such as mesylate, tosylate, and triflate; and sulfinyl groups, such as methylsulfinyl and phenylsulfinyl.

Ethynylphenylamidine Compound

The ethynylphenylamidine compounds represented by Formula (1) of the present invention are novel compounds in which an ethynyl group is bonded to the phenyl ring at the para-position with respect to an amidino group.

The ethynylphenylamidine compounds represented by Formula (1) have E- and Z-geometrical isomers of the amidino group, and the compounds of the present invention include each of these isomers and mixtures thereof. Moreover, depending on the type and combination of substituents, there may be isomers, such as stereoisomers, enantiomers, and tautomers; and the compounds of the present invention also include each of these isomers and mixtures thereof.

The ethynylphenylamidine compounds represented by Formula (1) have basicity, allowing them to form salts with, for example, mineral acids, such as hydrochloric acid, hydrobromic acid, and sulfuric acid; organic carboxylic acids, such as tartaric acid, formic acid, acetic acid, citric acid, fumaric acid, maleic acid, trichloroacetic acid, and trifluoroacetic acid; or sulfonic acids, such as methanesulfonic acid, benzenesulfonic acid, p-toluenesulfonic acid, mesitylenesulfonic acid, naphthalenesulfonic acid, and camphorsulfonic acid. The ethynylphenylamidine compounds represented by Formula (1) of the present invention also include these salts.

Preferred among the ethynylphenylamidine compounds represented by Formula (1) of the present invention are those wherein $R^3$ is hydrogen.

Preferred among the ethynylphenylamidine compounds represented by Formula (1) of the present invention are those wherein $R^1$ and $R^2$ are each $C_{1-12}$ alkyl, more preferably $C_{1-4}$ alkyl, and particularly preferably methyl or ethyl.

Preferred among the ethynylphenylamidine compounds represented by Formula (1) of the present invention are those wherein $R^4$ or $R^7$ are each halogen or $C_{1-4}$ alkyl, more preferably fluorine, chlorine, or methyl, and particularly preferably methyl.

Preferred among the ethynylphenylamidine compounds represented by Formula (1) of the present invention are those wherein $R^5$ and $R^7$ are each hydrogen; and $R^4$ and $R^6$ are each halogen or $C_{1-4}$ alkyl, more preferably fluorine, chlorine, or methyl, and particularly preferably methyl.

Preferred among the ethynylphenylamidine compounds represented by Formula (1) of the present invention are those wherein $R^6$ is hydrogen; $C_{1-12}$ alkyl optionally substituted on the alkyl group with one or more substituents independently selected from the group consisting of $C_{1-4}$ alkoxy, hydroxy, cyano, and phenyl; $C_{3-8}$ cycloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group; or —$(CH_2)$n-Si$(R^9)(R^{10})(R^{11})$ wherein $R^9$, $R^{10}$, and $R^{11}$ are each $C_{1-6}$ alkyl, and n is an integer of 0 or 1. More preferred are those wherein $R^8$ is $C_{1-12}$ alkyl optionally substituted on the alkyl group with one or more substituents independently selected from the group consisting of hydroxy, cyano, and phenyl; phenyl optionally substituted on the phenyl ring with one to five substituents selected from the group consisting of halogen, $C_{1-6}$ alkyl, and haloalkyl; or —$(CH_2)$n-Si$(R^9)(R^{10})(R^{11})$ wherein $R^9$, $R^{10}$, and $R^{11}$ are each $C_{1-6}$ alkyl, and n is an integer of 0 or 1. Particularly preferred are those wherein $R^8$ is $C_{1-6}$ alkyl, phenyl, or —$(CH_2)$n-Si$(R^9)(R^{10})(R^{11})$ wherein $R^9$, $R^{10}$, and $R^{11}$ are each $C_{1-6}$ alkyl, and n is an integer of 0 or 1. Specifically, the most preferred are those wherein $R^8$ is tert-butyl, phenyl, trimethylsilyl, triethylsilyl, triisopropylsilyl, tert-butyldimethylsilyl, or trimethylsilylmethyl.

Method for Producing Ethynylphenylamidine Compound

The ethynylphenylamidine compounds represented by Formula (1) of the present invention can be easily produced, for example, by the method shown in the following Reaction Scheme 1, 2, 3, or 4.

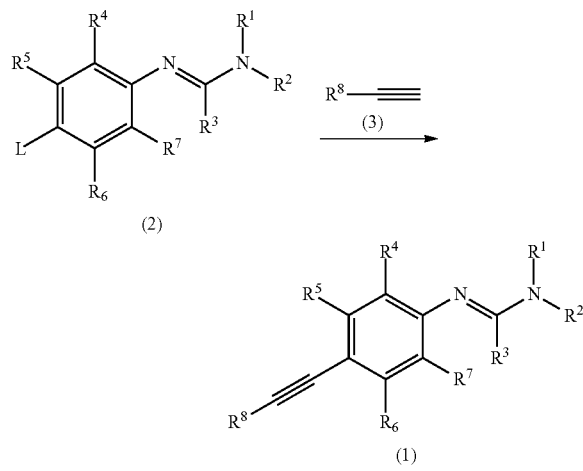

Reaction Scheme 1

(2)

(3)

(1)

wherein $R^1$, $R^2$, $R^3$, $R^4$, $R^5$, $R^6$, $R^7$, $R^8$, and L are as defined above.

In the method shown in Reaction Scheme 1, the ethynylphenylamidine compound represented by Formula (1) is produced by reacting a phenylamidine compound represented by Formula (2) with an acetylene compound represented by Formula (3) in the presence of a palladium catalyst and a base.

The reaction of the compound of Formula (2) and the compound of Formula (3) can be performed in an inert solvent, as necessary.

Examples of the inert solvent include aliphatic or cycloaliphatic hydrocarbon solvents, such as hexane, cyclohexane, and heptane; aromatic hydrocarbon solvents, such as benzene, chlorobenzene, nitrobenzene, toluene, and xylene; halogenated hydrocarbon solvents, such as methylene chloride, 1,2-dichloroethane, chloroform, and carbon tetrachloride; ether solvents, such as diethyl ether, diisopropyl ether, tetrahydrofuran, 1,4-dioxane, dimethoxyethane, diethylene glycol dimethyl ether, and methyl tert-butyl ether; ester solvents, such as methyl acetate and ethyl acetate; ketone solvents, such as acetone, methyl ethyl ketone, and cyclohexanone; amide solvents, such as N,N-dimethylformamide, N,N-dimethylacetamide, N-methylformanilide, N,N'-dimethylimidazolinone, and N-methylpyrrolidone; nitrile solvents, such as acetonitrile and propionitrile; sulfoxide solvents, such as dimethylsulfoxide; alcohol solvents, such as methanol, ethanol, n-propanol, isopropanol, n-butanol, isobutanol, s-butanol, tert-butanol, ethanediol, methoxy ethanol, ethoxy ethanol, diethylene glycol monomethyl ether, and diethylene glycol monoethyl ether; and water. These solvents can be used singly or in combination of two or more.

The solvent is generally used in an amount of about 1 to 500 parts by weight, and preferably about 5 to 100 parts by weight, per part by weight of the phenylamidine compound represented by Formula (2).

Examples of the palladium catalyst used in the above reaction include palladium chloride, palladium acetate, tetrakis(triphenylphosphine)palladium, dichlorobis(triphenylphosphine)palladium, 1,1'-bis(diphenylphosphino)ferrocenepalladium, bis(benzylideneacetone)palladium, palladium acetate-triphenylphosphine, palladium acetate-tricyclohexylphosphine, dichloropalladium-1,1'-bis(dicyclohexylphosphino)ferrocene, palladium/carbon, and the like. When a palladium catalyst is in the form of a complex, such a complex may be used in an isolated form or may be formed in the reaction solvent. Among these palladium catalysts, palladium chloride, palladium acetate, tetrakis(triphenylphosphine)palladium, dichlorobis(triphenylphosphine)palladium, and palladium/carbon are preferably used; and palladium chloride, palladium acetate, and dichlorobis(triphenylphosphine)palladium are particularly preferably used.

The palladium catalyst is generally used in an amount of 0.005 to 0.5 mol, and preferably 0.002 to 0.05 mol, per mol of the phenylamidine compound represented by Formula (2).

Examples of the base used in the above reaction include inorganic bases, such as sodium carbonate, potassium carbonate, sodium hydrogen carbonate, and other alkali metal carbonates; calcium carbonate and other alkaline earth metal carbonates; sodium hydroxide, potassium hydroxide, and other alkali metal hydroxides; sodium hydride, potassium hydride, and other alkali metal hydrides; and organic bases, such as propylamine, butylamine, diethylamine, diisopropylamine, diisopropylethylamine, triethylamine, tributylamine, piperidine, pyrrolidine, diazabicyclooctane, diazabicycloundecene, and other amines; pyridine, 2-picoline, 3-picoline, 4-picoline, and other pyridines; sodium methoxide, sodium ethoxide, potassium tert-butoxide, sodium tert-butoxide, and other alkali metal alkoxides; and the like. These bases can be used singly or in combination of two or more. Preferred among these bases are alkali metal carbonates, such as sodium carbonate, potassium carbonate, and sodium hydrogen carbonate; amines, such as propylamine, butylamine, diethylamine, diisopropylamine, diisopropylethylamine, triethylamine, tributylamine, piperidine, pyrrolidine, diazabicyclooctane, and diazabicycloundecene; and pyridines, such as pyridine, 2-picoline, 3-picoline, and 4-picoline. Particularly preferred are potassium carbonate, sodium hydrogen carbonate, diethylamine, triethylamine, and diisopropylethylamine.

The base is generally used in an amount of 0.1 to 100 equivalents, and preferably 1 to 3 equivalents, per equivalent of the phenylamidine compound represented by Formula (2).

Although the proportion of the phenylamidine compound represented by Formula (2) and the acetylene compound represented by Formula (3) used in the above reaction can be suitably selected from a wide range, the amount of the latter compound is preferably 0.5 mol or more, and more preferably 1 to 3 mol, per mol of the former compound.

It is preferable that a copper catalyst is present in the above reaction system. Examples of usable copper catalysts include copper iodide, copper bromide, copper chloride, copper oxide, copper cyanide, etc., with copper iodide being preferred. The amount of copper catalyst used is generally 0.005 to 0.5 mol, and preferably 0.001 to 0.1 mol, per mol of the phenylamidine compound represented by Formula (2).

The above reaction is generally carried out at a temperature ranging from −78° C. to the boiling point of the solvent used, preferably 0° C. to the boiling point of the solvent, and more preferably 10° C. to 100° C. Further, the reaction is preferably carried out in an inert gas atmosphere, such as nitrogen or argon.

The reaction time of the reaction cannot be categorically determined because it varies with the reaction temperature, the amount of the substrate used, and other conditions; however, the reaction is generally completed in about 0.5 to 72 hours.

sented by Formula (4) with an ortho-ester compound represented by Formula (5) in the presence of an acid, and then reacting the produced compound with an amine compound represented by Formula (6).

The above reaction can be performed in a solvent, as necessary. As the solvent, any inert solvent can be used without difficulty. Examples thereof include aliphatic or cycloaliphatic hydrocarbon solvents, such as hexane, cyclohexane, and heptane; aromatic hydrocarbon solvents, such as benzene, chlorobenzene, nitrobenzene, toluene, and xylene; halogenated hydrocarbon solvents, such as methylene chloride, 1,2-dichloroethane, chloroform, and carbon tetrachloride; ether solvents, such as diethyl ether, diisopropyl ether, tetrahydrofuran, 1,4-dioxane, dimethoxyethane, diethylene glycol dimethyl ether, and methyl tert-butyl ether; ester solvents, such as methyl acetate and ethyl acetate; amide solvents, such as N,N-dimethylformamide, N,N-dimethylacetamide, N-methylformanilide, N,N'-dimethylimidazolinone, and N-methylpyrrolidone; nitrile solvents, such as acetonitrile and propionitrile; sulfoxide solvents, such as dimethylsulfoxide; sulfone solvents, such as sulfolane; alcohol solvents, such as methanol, ethanol, n-propanol, isopropanol, n-butanol, isobutanol, sec-butanol, tert-butanol, ethanediol, methoxyethanol, ethoxyethanol, diethylene glycol monomethyl ether, and diethylene glycol monoethyl ether; and water. These solvents can be used singly or in combination of two or more.

The solvent is generally used in an amount of about 1 to 500 parts by weight, and preferably about 5 to 100 parts by weight, per part by weight of the ethynylphenylamidine compound represented by Formula (4).

The ortho-ester compound represented by Formula (5) can be selected from a wide range of known ortho-ester compounds. Specific examples thereof include ethyl orthoformate, methyl orthoformate, propyl orthoformate, isopropyl orthoformate, and n-butyl orthoformate. Among these, ethyl orthoformate, methyl orthoformate, etc., can be preferably used.

The acid used in the reaction of the ethynylaniline compound represented by Formula (4) and the ortho-ester compound represented by Formula (5) may be an inorganic or organic acid that is generally used in this kind of reaction. For example, p-toluenesulfonic acid, benzenesulfonic acid, methanesulfonic acid, hydrochloric acid, or sulfuric acid can be preferably used. The amount of the acid to be used is generally a catalytic amount.

The reaction of the ethynylaniline compound represented by Formula (4) and the ortho-ester compound represented by Formula (5) is generally performed at 0° C. to 150° C., and preferably 100° C. to 120° C., using the ortho-ester compound represented by Formula (5) generally in an amount of 0.8 to 80 mol, and preferably 5 to 50 mol, per mol of the ethynylaniline compound represented by Formula (4).

The reaction time of the reaction cannot be categorically determined because it varies with the reaction temperature, the amount of the substrate used, and other conditions; however, the reaction is generally completed in about 0.5 to 72 hours.

The reaction of the reaction product of the ethynylaniline compound represented by Formula (4) and the ortho-ester compound represented by Formula (5), with the amine compound represented by Formula (6) may be performed after isolation of the reaction product; however, the reaction can generally be performed by directly reacting the amine compound represented by Formula (6) in the reaction solution of the ethynylaniline compound represented by Formula (4) and

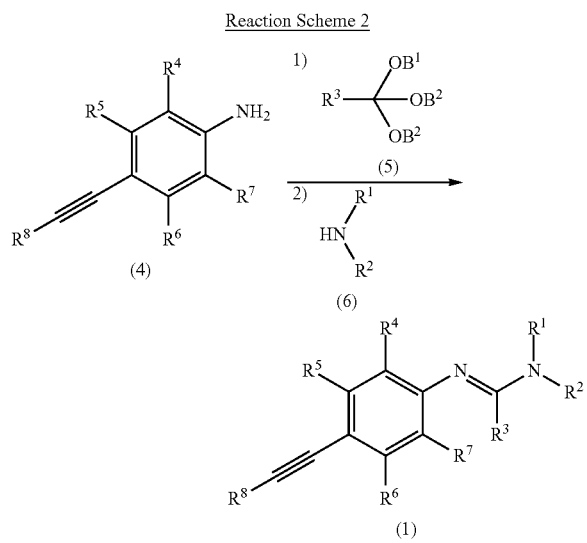

wherein $R^1$, $R^2$, $R^3$, $R^4$, $R^5$, $R^6$, $R^7$, $R^8$, $B^1$, and $B^2$ are as defined above.

In the method shown in Reaction Scheme 2, the ethynylphenylamidine compound represented by Formula (1) is produced by reacting an ethynylaniline compound reprethe ortho-ester compound represented by Formula (5), without isolation of the reaction product from the reaction solution.

As for the amount of the amine compound used, the amount of the ortho-ester compound represented by Formula (5) is generally 0.8 to 80 mol, and preferably 5 to 50 mol, per mol of the ethynylaniline compound represented by Formula (4).

This reaction is generally carried out at 0° C. to 150° C., and preferably 10° C. to 50° C.

The reaction time of the reaction cannot be categorically determined because it varies with the reaction temperature, the amount of the substrate used, and other conditions; however, the reaction is generally completed in about 0.5 to 72 hours.

Reaction Scheme 3

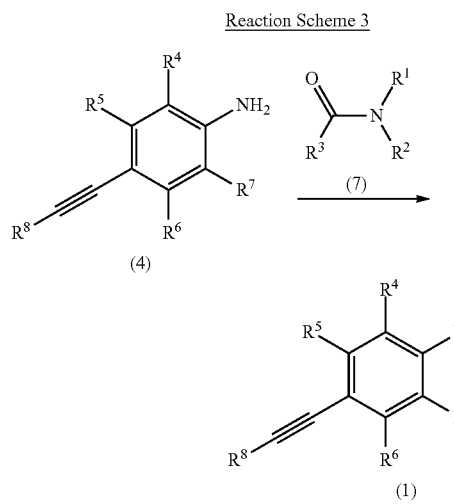

wherein $R^1$, $R^2$, $R^3$, $R^4$, $R^5$, $R^6$, $R^7$, and $R^8$ are as defined above.

In the method shown in Reaction Scheme 3, the ethynylphenylamidine compound represented by Formula (1) is produced by reacting an ethynylaniline compound represented by Formula (4) with an amide compound represented by Formula (7) in the presence of a halogenating agent.

The above reaction can be performed in a solvent, as necessary. As the solvent, any inert solvent can be used without difficulty. Examples thereof include aliphatic or cycloaliphatic hydrocarbon solvents, such as hexane, cyclohexane, and heptane; aromatic hydrocarbon solvents, such as benzene, chlorobenzene, nitrobenzene, toluene, and xylene; halogenated hydrocarbon solvents, such as methylene chloride, 1,2-dichloroethane, chloroform, and carbon tetrachloride; ether solvents, such as diethyl ether, diisopropyl ether, tetrahydrofuran, 1,4-dioxane, dimethoxyethane, diethylene glycol dimethyl ether, and methyl tert-butyl ether; ester solvents, such as methyl acetate and ethyl acetate; amide solvents, such as N,N-dimethylformamide, N,N-dimethylacetamide, N-methylformanilide, N,N'-dimethylimidazolinone, and N-methylpyrrolidone; nitrile solvents, such as acetonitrile and propionitrile; sulfoxide solvents, such as dimethylsulfoxide; sulfone solvents, such as sulfolane; alcohol solvents, such as methanol, ethanol, n-propanol, isopropanol, n-butanol, isobutanol, sec-butanol, tert-butanol, ethanediol, methoxyethanol, ethoxyethanol, diethylene glycol monomethyl ether, and diethylene glycol monoethyl ether; and water. These solvents can be used singly or in combination of two or more.

The solvent is generally used in an amount of about 1 to 500 parts by weight, and preferably about 5 to 100 parts by weight, per part by weight of the ethynylphenylamidine compound represented by Formula (4).

The above reaction is performed in the presence of a halogenating agent. The halogenating agent can be selected from a wide range of known halogenating agents. Examples thereof include phosphorus pentachloride, phosphorus trichloride, phosphorus oxychloride, thionyl chloride, and the like.

The amount of the halogenating agent to be used is generally 0.8 to 100 mol, and preferably 1 to 20 mol, per mol of the ethynylaniline compound represented by Formula (4).

The above reaction is generally performed at 0° C. to 150° C., and preferably 100° C. to 120° C., using the amide compound represented by Formula (7) generally in an amount of 0.8 to 80 mol, and preferably 1 to 10 mol, per mol of the ethynylaniline compound represented by Formula (4).

The reaction time of the reaction cannot be categorically determined because it varies with the reaction temperature, the amount of the substrate used, and other conditions; however, the reaction is generally completed in about 0.5 to 72 hours.

Reaction Scheme 4

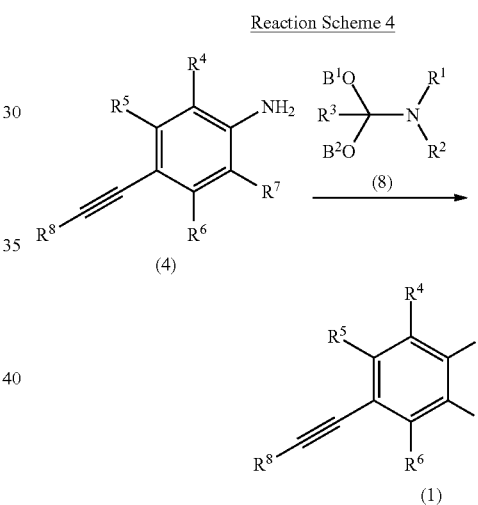

wherein $R^1$, $R^2$, $R^3$, $R^4$, $R^5$, $R^6$, $R^7$, $R^8$, $B^1$, and $B^2$ are as defined above.

In the method shown in Reaction Scheme 4, the ethynylphenylamidine compound represented by Formula (1) is produced by reacting an ethynylaniline compound represented by Formula (4) with an aminoacetal compound represented by Formula (8).

The above reaction can be performed in a solvent, as necessary. As the solvent, any inert solvent can be used without difficulty. Examples thereof include aliphatic or cycloaliphatic hydrocarbon solvents, such as hexane, cyclohexane, and heptane; aromatic hydrocarbon solvents, such as benzene, chlorobenzene, nitrobenzene, toluene, and xylene; halogenated hydrocarbon solvents, such as methylene chloride, 1,2-dichloroethane, chloroform, and carbon tetrachloride; ether solvents, such as diethyl ether, diisopropyl ether, tetrahydrofuran, 1,4-dioxane, dimethoxyethane, diethylene glycol dimethyl ether, and methyl tert-butyl ether; ester solvents, such as methyl acetate and ethyl acetate; amide solvents, such as N,N-dimethylformamide, N,N-dimethylacetamide, N-methylformanilide, N,N'-dimethylimidazolinone, and N-methylpyrrolidone; nitrile solvents, such as acetonitrile and propionitrile; sulfoxide solvents, such as dimethylsulfoxide; sulfone solvents, such as sulfolane; alcohol solvents, such as methanol, ethanol, n-propanol, isopropanol, n-butanol, isobutanol, sec-butanol, tert-butanol, ethanediol, methoxyethanol, ethoxyethanol, diethylene glycol monomethyl ether, and diethylene glycol monoethyl ether; and water. These solvents can be used singly or in combination of two or more.

The solvent is generally used in an amount of about 1 to 500 parts by weight, and preferably about 5 to 100 parts by weight, per part by weight of the ethynylphenylamidine compound represented by Formula (4).

The above reaction is generally performed at 0° C. to 150° C., and preferably 20° C. to 120° C., using the aminoacetal compound represented by Formula (8) generally in an amount of 0.8 to 80 mol, and preferably 1 to 10 mol, per mol of the ethynylaniline compound represented by Formula (4).

The reaction time of the reaction cannot be categorically determined because it varies with the reaction temperature, the amount of the substrate used, and other conditions; however, the reaction is generally completed in about 0.5 to 72 hours.

The phenylamidine compound represented by Formula (2) used as a starting material in Reaction Scheme 1 above can be easily produced by performing the same reaction as in Reaction Scheme 2, 3, or 4 using an aniline compound represented by Formula (9) in place of the ethynylaniline compound represented by Formula (4).

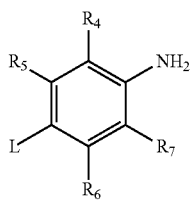

(9)

wherein $R^4$, $R^5$, $R^6$, $R^7$, and L are as defined above.

The ethynylaniline compound represented by Formula (4) used as a starting material in Reaction Schemes 2, 3, and 4 above can be easily produced by performing the same reaction as in Reaction Scheme 1 using the aniline compound represented by Formula (9) in place of the phenylamidine compound represented by Formula (2).

The ethynylaniline compound represented by Formula (4) is a novel compound that is not disclosed in any documents, and is a useful compound that can be suitably used as a production intermediate of the ethynylphenylamidine compound represented by Formula (1).

The aniline compound represented by Formula (9) can be easily produced by making full use of known methods, and is a known, commercially available compound.

The target compound obtained in each of the above reactions can be easily isolated from the reaction mixture by a generally used isolation method, such as organic solvent extraction, chromatography, recrystallization, or distillation, and further purified by a general purification method.

The ethynylphenylamidine compounds represented by Formula (1) of the present invention have an excellent fungicidal activity and a wide fungicidal spectrum, and can be used to control agricultural and horticultural diseases, such as blast, brown spot, sheath blight, and bakanae disease of rice; powdery mildew, scab, rust, snow mold, loose smut, eyespot, leaf blotch, and glume blotch of wheat; melanose and scab of citrus; blossom blight, powdery mildew, *Alternaria* leaf spot, and scab of apple; frogeye, scab, and black spot of pear; brown rot, scab, and *Phomopsis* rot of peach; anthracnose, ripe rot, powdery mildew, and downy mildew of grape; anthracnose and brown stem rot of Japanese persimmon; anthracnose, powdery mildew, gummy stem blight, and downy mildew of cucurbit; early blight, leaf mold, and late blight of tomato; gray blight and anthracnose of tea; *Alternaria* leaf spot of crucifer; late blight and early blight of potato; powdery mildew of strawberry; and gray mold and stem rot of various crops. Particularly, the compounds of the present invention can be suitably used for various powdery mildews of cereals and vegetables.

Moreover, the ethynylphenylamidine compounds represented by Formula (1) of the present invention can also be effectively used to control soil diseases caused by plant pathogens, such as *Fusarium*, *Pythium*, *Rhizoctonia*, *Verticillium*, and *Plasmodiophora*.

Furthermore, the ethynylphenylamidine compounds represented by Formula (1) of the present invention include compounds having an excellent vaporization effect. Such compounds exhibit a more excellent disease-control effect.

The ethynylphenylamidine compounds represented by Formula (1) of the present invention may be directly used as fungicides without addition of other components; however, they can be generally mixed with various liquid, solid, or gaseous carriers, optionally followed by the addition of surfactants and other formulation aids, to form various formulations, such as oil solutions, emulsifiable concentrates, wettable powders, dry flowables, flowables, water soluble powders, granules, fine granules, dispersible granules, dust formulations, coating compositions, spray preparations, aerosols, microcapsules, fumigants, smoking formulations, and the like.

In these formulations, the content of the ethynylphenylamidine compound represented by Formula (1) is not particularly limited, and can be suitably selected from a wide range depending on various conditions, such as dosage form, type of target diseases and crops, degree of disease, application site, application Lime, application method, drugs to be used in combination (e.g., insecticides, miticides, nematocides, fungicides, herbicides, plant growth agents, synergists, and soil conditioners), and amount and type of fertilizer used. The content of the ethynylphenylamidine compound represented by Formula (1) may be generally about 0.01 to 95 wt %, and preferably about 0.1 to 50 wt %, based on the total weight of the fungicide.

Any known carriers that are commonly used in this field can be used.

Examples of solid carriers used in the preparation of these formulations include clays, such as kaolin clay, diatomaceous earth, bentonite, Fubasami clay, and acid clay; talcs; inorganic minerals, such as ceramics, cerite, quartz, sulfur, activated carbon, silica carbonate, and hydrated silica; fine powders and granules of fertilizers (e.g., ammonium sulfate, ammonium phosphate, ammonium nitrate, urea, and ammonium chloride); and the like.

Examples of liquid carriers include water; alcohols, such as methanol and ethanol; ketones, such as acetone, methyl ethyl ketone, and methyl isobutyl ketone; aliphatic or alicyclic hydrocarbons, such as n-hexane, cyclohexane, kerosene, and light oil; aromatic hydrocarbons, such as benzene, chlorobenzene, toluene, xylene, and naphthalene; esters, such as ethyl acetate and butyl acetate; nitriles, such as acetonitrile and isobutyronitrile; ethers, such as diisopropyl ether and dioxane; acid amides, such as N,N-dimethylformamide, N,N- dimethylacetamide, N-methylpyrrolidone, and N,N'-dimethylimidazolinone; halogenated hydrocarbons, such as dichloromethane, trichloroethane, and carbon tetrachloride; dimethylsulfoxide; vegetable oils, such as soybean oil, cottonseed oil, olive oil, coconut oil, rapeseed oil, sesame oil, corn oil, and castor oil; and the like.

Usable gaseous carriers are those generally used as propellants. Examples thereof include butane gas, liquefied petroleum gas, dimethyl ether, carbon dioxide gas, and the like.

Examples of surfactants include nonionic surfactants, anionic surfactants, and the like.

Specific examples of nonionic surfactants include sugar ester-type nonionic surfactants, such as sorbitan fatty acid ester and polyoxyethylene sorbitan fatty acid ester; fatty acid ester-type nonionic surfactants, such as polyoxyethylene fatty acid ester; vegetable oil-type nonionic surfactants, such as polyoxyethylene castor oil; alcohol-type nonionic surfactants, such as polyoxyethylene alkyl ether; alkylphenol-type nonionic surfactants, such as polyoxyethylene alkyl ($C_{8-12}$) phenyl ether/formalin condensate; polyoxyethylene/polyoxypropylene block polymer-type nonionic surfactants, such as polyoxyethylene/polyoxypropylene block polymers; polyaromatic ring-type nonionic surfactants, such as phenylphenyl ether; and the like.

Specific examples of anionic surfactants include sulfonate-type anionic surfactants, such as alkylbenzene sulfonate, alkyl sulfosuccinate, and allyl sulfonate; sulfate-type anionic surfactants, such as alkyl sulfate and polyoxyethylene alkyl sulfate; lignin sulfite; and the like.

Examples of formulation aids include fixing agents, dispersing agents, thickeners, preservatives, anti-freezing agents, stabilizers, adjuvants, and the like.

Examples of fixing agents and dispersing agents include casein, gelatin, polysaccharides (e.g., starch, gum arabic, cellulose derivatives, and alginic acid), lignin derivatives, bentonite, sugars, water-soluble synthetic polymers (e.g., polyvinyl alcohol, polyvinyl pyrrolidone, and polyacrylic acids), and the like.

Examples of thickeners include water-soluble polymer compounds, such as xanthan gum and carboxymethyl cellulose; high-purity bentonite, white carbon, and the like.

Examples of preservatives include sodium benzoate, p-hydroxybenzoic acid ester, and the like.

Examples of anti-freezing agents include ethylene glycol, diethylene glycol, and the like.

Examples of stabilizers include PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surfactants, fatty acids or esters thereof, and the like.

Examples of adjuvants include soybean oil, corn oil, and like vegetable oils, machine oil, glycerin, polyethylene glycol, and the like.

Such formulations may be colored with an organic or inorganic dye.

In addition, the compounds of the present invention may be formed into formulations by mixing them with other insecticides, nematocides, miticides, fungicides, antiviral agents, attractants, herbicides, plant growth regulators, synergists (e.g., piperonyl butoxide), soil conditioners, etc. Alternatively, in order to obtain a more excellent effect, the fungicide of the present invention can be used in combination with each of the above agents at the point of use.

When the compound of the present invention is used as an agricultural and horticultural fungicide, the amount of application thereof is not particularly limited and can be suitably selected from a wide range depending on various conditions, such as amount of active ingredient, dosage form, type of target diseases and crops, degree of disease, application site, application time, application method, drugs to be used in combination (e.g., insecticides, miticides, nematocides, fungicides, herbicides, plant growth agents, synergists, and soil conditioners), and amount and type of fertilizer used; however, the amount of application is generally about 0.001 g to 100 g per 100 $m^2$. When emulsifiable concentrates, wettable powders, flowables, etc., are used after they are diluted with water, the concentration of application is generally about 0.1 to 1,000 ppm, and preferably about 1 to 500 ppm. Granules, dust formulations, etc., can be used as they are without being diluted.

Advantageous Effects of Invention

The ethynylphenylamidine compounds represented by Formula (1) of the present invention have an excellent fungicidal activity and a wide fungicidal spectrum, and thus have an excellent control effect on agricultural and horticultural diseases. Therefore, the ethynylphenylamidine compounds represented by Formula (1) of the present invention can be suitably used as fungicides, particularly agricultural and horticultural fungicides.

DESCRIPTION OF EMBODIMENTS

The present invention is described in more detail below with reference to Reference Examples, Production Examples, Formulation Examples, and Test Examples; however, the present invention is not limited thereto.

Reference Example 1

Production of N,N-dimethyl-N'-(4-iodo-2-methylphenyl)formamidine (Compound 2-1)

Methyl orthoformate (105 g) and 0.8 g of p-toluenesulfonic acid monohydrate were added to 10.0 g of 4-iodo-2-methylaniline, and the mixture was heated under reflux for 12 hours. The reaction solution was concentrated under reduced pressure, and the resulting residue was dissolved in 50 ml of dichloromethane. A 50% dimethylamine aqueous solution (7.70 g) was added thereto, and the mixture was stirred at 25° C. for 15 hours. The reaction solution was concentrated under reduced pressure, and the obtained residue was purified by silica gel column chromatography (n-hexane:ethyl acetate=4:1), thereby obtaining 6.80 g of N,N-dimethyl-N'-(4-iodo-2-methylphenyl)formamidine (Compound 2-1).

$^1$H NMR (300 MHz, CDCl$_3$): 2.21 (s, 3H), 3.00 (s, 6H), 6.48 (d, 1H), 7.34-7.37 (m, 2H), 7.43 (s, 1H)

Reference Example 2

Production of N-ethyl-N-methyl-N'-(4-iodo-2-methylphenyl)formamidine (Compound 2-2)

Methyl orthoformate (24.1 g) and 0.19 g of p-toluenesulfonic acid monohydrate were added to 2.30 g of 4-iodo-2-methylaniline, and the mixture was heated under reflux for 12 hours. The reaction solution was concentrated under reduced pressure, and the resulting residue was dissolved in 20 ml of dichloromethane. N-ethyl-methylamine (1.17 g) was added thereto, and the mixture was stirred at 25° C. for 15 hours. The reaction solution was concentrated under reduced pressure, and the obtained residue was purified by silica gel column chromatography (n-hexane:ethyl acetate=4:1), thereby obtaining 1.80 g of N-ethyl-N-methyl-N'-(4-iodo-2-methylphenyl)formamidine (Compound 2-2).

$^1$H NMR (300 MHz, CDCl$_3$): 1.20 (t, 3H), 2.20 (s, 3H), 2.98 (s, 3H), 3.30 (brs, 2H), 6.48 (d, 1H), 7.35-7.37 (m, 2H), 7.43 (s, 1H)

Production Example 1

Production of 4-(2-phenyl-1-ethynyl)aniline (Compound 4-1)

Dimethylformamide (10 ml), 10 ml of triethylamine, 0.93 g of phenylacetylene, 0.32 g of palladium chloride-ditriphenylphosphine complex, and 0.09 g of copper iodide were added to 1.0 g of 4-iodoaniline, and the mixture was stirred at 50° C. for 12 hours. After completion of the reaction, water was added to the reaction solution, and extraction was performed 3 times with ethyl acetate. The organic layer was collected, washed with a saturated aqueous sodium chloride solution, and dried over anhydrous magnesium sulfate. The solvent was removed under reduced pressure. The obtained residue was purified by silica gel column chromatography (n-hexane:ethyl acetate=3:1), thereby obtaining 0.50 g of 4-(2-phenyl-1-ethynyl)aniline (Compound 4-1).

Production Example 2

Production of 2,5-dimethyl-4-(3,3-dimethyl-1-butynyl) aniline (Compound 4-25)

Tetrahydrofuran (5 ml), 5 ml of triethylamine, 216 mg of tert-butylacetylene, 71 mg of palladium chloride-ditriphenylphosphine complex, and 19 mg of copper iodide were added to 0.5 q of 2,5-dimethyl-4-iodoaniline, and the mixture was stirred at 50° C. for 15 hours. After completion of the reaction, water was added to the reaction solution, and extraction was performed 3 times with ethyl acetate. The organic layer was collected, washed with a saturated aqueous sodium chloride solution, and dried over anhydrous magnesium sulfate. The solvent was removed under reduced pressure. The obtained residue was purified by silica gel column chromatography (n-hexane:ethyl acetate=10:1), thereby obtaining 0.31 g of 2,5-dimethyl-4-(3,3-dimethyl-1-butynyl)aniline (Compound 4-25).

Production Example 3

Production of 2,5-dimethyl-4-(2-trimethylsilyl-1-ethynyl)aniline (Compound 4-27)

Tetrahydrofuran (100 ml), 100 ml of triethylamine, 7.6 g of trimethylsilyl acetylene, 1.25 g of palladium chloride-ditriphenylphosphine complex, and 0.34 g of copper iodide were added to 14.7 g of 2,5-dimethyl-4-iodoaniline, and the mixture was stirred at 50° C. for 15 hours. After completion of the reaction, water was added to the reaction solution, and extraction was performed 3 times with ethyl acetate. The organic layer was collected, washed with a saturated aqueous sodium chloride solution, and dried over anhydrous magnesium sulfate. The solvent was removed under reduced pressure. The obtained residue was purified by silica gel column chromatography (n-hexane:ethyl acetate=5:1), thereby obtaining 9.8 g of 2,5-dimethyl-4-(2-trimethylsilyl-1-ethynyl)aniline (Compound 4-27).

Production Example 4

Production of N,N-dimethyl-N'-[2-methyl-4-(2-trimethylsilyl-1-ethynyl)phenyl]formamidine (Compound 49)

Dimethylformamide (10 ml), 10 ml of triethylamine, 0.33 g of trimethylsilyl acetylene, 0.11 g of palladium chloride-ditriphenylphosphine complex, and 0.03 g of copper iodide were added to 0.50 g of the N,N-dimethyl-N'-(4-iodo-2-methylphenyl)formamidine (Compound 2-1) produced in Reference Example 1, and the mixture was stirred at 80° C. for 12 hours. After completion of the reaction, water was added to the reaction solution, and extraction was performed 3 times with ethyl acetate. The organic layer was collected, washed with a saturated aqueous sodium chloride solution, and dried over anhydrous magnesium sulfate. The solvent was removed under reduced pressure. The obtained residue was purified by silica gel column chromatography (n-hexane:ethyl acetate=3:1), thereby obtaining 0.20 g of N,N-dimethyl-N'-[2-methyl-4-(2-trimethylsilyl-1-ethynyl)phenyl]formamidine (Compound 49).

Production Example 5

Production of N-ethyl-N-methyl-N'-[2-methyl-4-(3,3-dimethyl-1-butynyl)phenyl]formamidine (Compound 66)

Dimethylformamide (10 ml), 10 ml of triethylamine, 0.27 g of tert-butylacetylene, 0.11 g of palladium chloride-ditriphenylphosphine complex, and 0.03 g of copper iodide were added to 0.50 g of the N-ethyl-N-methyl-N'-(4-iodo-2-methylphenyl)formamidine (Compound 2-2) produced in Reference Example 2, and the mixture was stirred at 80° C. for 12 hours. After completion of the reaction, water was added to the reaction solution, and extraction was performed 3 times with ethyl acetate. The organic layer was collected, washed with a saturated aqueous sodium chloride solution, and dried over anhydrous magnesium sulfate. The solvent was removed under reduced pressure. The obtained residue was purified by silica gel column chromatography (n-hexane:ethyl acetate=3:1), thereby obtaining 0.10 g of N-ethyl-N-methyl-N'-[2-methyl-4-(3,3-dimethyl-1-butynyl)phenyl]formamidine (Compound 66).

Production Example 6

Production of N,N-dimethyl-N'-[(4-(phenyl-1-ethynyl)phenyl]formamidine (Compound 5)

Methyl orthoformate (6.32 g) and 0.05 g of p-toluenesulfonic acid monohydrate were added to 0.50 g of the 4-(2-phenyl-1-ethynyl)aniline (Compound 4-1) produced in Production Example 1, and the mixture was heated under reflux for 12 hours. The reaction solution was concentrated under reduced pressure, and the resulting residue was dissolved in 200 ml of dichloromethane. A 50% dimethylamine aqueous solution (0.47 g) was added thereto, and the mixture was stirred at 25° C. for 16 hours. The reaction solution was concentrated under reduced pressure, and the obtained residue was purified by silica gel column chromatography (n-hexane:ethyl acetate=2:1), thereby obtaining 0.06 g of N,N-dimethyl-N'-[(4-(phenyl-1-ethynyl)phenyl]formamidine (Compound 5).

Production Example 7

Production of N,N-dimethyl-N'-[2,5-dimethyl-4-(3,3-dimethyl-1-butynyl)phenyl]formamidine (Compound 52)

Phosphorus oxychloride (182 mg) was added to a mixture of 5 ml of dichloromethane and 145 mg of N,N-dimethylformamide at 25° C. After the mixture was stirred at 25° C. for 1 hour, 1 ml of a methylene chloride solution containing 200 mg of the 2,5-dimethyl-4-(3,3-dimethyl-1-butynyl)aniline (Compound 4-25) produced in Production Example 2 was added dropwise thereto. The mixture was stirred at 25° C. for 2.5 hours, and the reaction solution was then poured into ice water. The pH was adjusted to 11 with an aqueous 1 N potassium hydroxide solution, and extraction was performed 3 time with dichloromethane. The organic layer was collected, washed with a saturated aqueous sodium chloride solution, and dried over anhydrous magnesium sulfate. The solvent was removed under reduced pressure. The obtained residue was purified by silica gel column chromatography (n-hexane:ethyl acetate=3:1), thereby obtaining 30 mg of N,N-dimethyl-N'-[2,5-dimethyl-4-(3,3-dimethyl-1-butynyl)phenyl]formamidine (Compound 52).

Production Example 8

Production of N,N-dimethyl-N'-[2,5-dimethyl-4-(2-trimethylsilyl-1-ethynyl)phenyl]formamidine (Compound 59)

N,N-dimethylformamide dimethyl acetal (5.97 g) and 10 ml of toluene were added to 1.09 g of the 2,5-dimethyl-4-(2-trimethylsilyl-1-ethynyl)aniline (Compound 4-27) produced in Production Example 3, and the mixture was stirred at 110° C. for 9 hours. The reaction solution was concentrated under reduced pressure, and the obtained residue was purified by silica gel column chromatography (n-hexane:ethyl acetate=5:1), thereby obtaining 0.56 g of N,N-dimethyl-N'-[2,5-dimethyl-4-(2-trimethylsilyl-1-ethynyl)phenyl]formamidine (Compound 59).

Production Example 9

Production of N-ethyl-N-methyl-N'-[2,5-dimethyl-4-(2-trimethylsilyl-1-ethynyl)phenyl]formamidine (Compound 123)

Methyl orthoformate (97.6 g) and 1.58 g of p-toluenesulfonic acid monohydrate were added to 20.0 g of the 2,5-dimethyl-4-(2-trimethylsilyl-1-ethynyl)aniline (Compound 4-27) produced in Production Example 3, and the mixture was heated under reflux for 12 hours. The reaction solution was concentrated under reduced pressure, and the obtained residue was dissolved in 100 ml of dichloromethane. N-ethylmethylamine (4.98 g) was added thereto, and the mixture was stirred at 25° C. for 12 hours. The reaction solution was concentrated under reduced pressure, and the obtained residue was purified by silica gel column chromatography (toluene:acetonitrile:triethylamine=50:1:0.1), thereby obtaining 14.5 g of N-ethyl-N-methyl-N'-[2,5-dimethyl-4-(2-trimethylsilyl-1-ethynyl)phenyl]formamidine (Compound 123).

Production Example 10

Production of N-ethyl-N-methyl-W-[2,5-dimethyl-4-(2-trimethylsilyl-1-ethynyl)phenyl]formamidine hydrochloride (Compound 162)

The N-ethyl-N-methyl-N'-[2,5-dimethyl-4-(2-trimethylsilyl-1-ethynyl)phenyl]formamidine (Compound 123) (400 mg) produced in Production Example 9 was dissolved in 5 ml of diethyl other, 700 mg of hydrochloric acid-ether solution was added under ice bath, and the mixture was stirred at 25° C. for 30 minutes. The reaction solution was concentrated under reduced pressure, and the obtained residue crystals were washed with a diethyl ether, thereby obtaining 412 mg of N-ethyl-N-methyl-N'-[2,5-dimethyl-4-(2-trimethylsilyl-1-ethynyl)phenyl]formamidine hydrochloride (Compound 162).

Production Example 11

Production of N-ethyl-N-methyl-N'-[2,5-dimethyl-4-(2-trimethylsilyl-1-ethynyl)phenyl]formamidine(+)-camphorsulfonate (compound 174)

The N-ethyl-N-methyl-N'-[2,5-dimethyl-4-(2-trimethylsilyl-1-ethynyl)phenyl]formamidine (Compound 123) produced in Production Example 9 was dissolved in 10 ml of hexane, 405 mg of (+)-camphorsulfonic acid was added, and the mixture was stirred at 25° C. for 30 minutes. The reaction solution was transferred to an ice bath and stirred for 30 minutes. The reaction solution was concentrated under reduced pressure, and the obtained residue crystals were washed with a diethyl ether, thereby obtaining 710 mg of N-ethyl-N-methyl-N'-[2,5-dimethyl-4-(2-trimethylsilyl-1-ethynyl)phenyl]formamidine(+) camphorsulfonate (Compound 174).

Tables 1 to 4 show the ethynylaniline compounds represented by Formula (4) produced by the methods shown in Production Examples 1 to 3, and $^1$H-NMR data of the compounds. Tables 5 to 25 show the ethynylphenylamidine compounds represented by Formula (1) produced by the methods shown in Production Examples 4 to 11, and the physical properties of the compounds.

The abbreviations used in the tables and their explanations are shown below:

Me: methyl

Et: ethyl n-Pr: n-propyl i-Pr: isopropyl c-Pr: cyclopropyl n-Bu: n-butyl i-Bu: isobutyl t-Bu: tert-butyl n-Pen: n-pentyl n-Hex: n-hexyl c-Hex: cyclohexyl Ph: phenyl Ts: p-toluenesulfonyl As for the substituted phenyl groups, for example, 3-trifluoromethylphenyl is expressed as Ph-3-$CF_3$, 4-methoxy-2-methylphenyl as Ph-2-Me-4-OMe, and 2,4,5-trimethylphenyl as Ph-2,4,5-$Me_3$. Other substituents are also expressed in the same manner.

The $^1$H-NMR spectra were measured relative to tetramethylsilane (TMS) as a standard.

TABLE 1

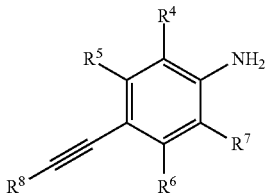

(4)

| Compd. No. | R⁴ | R⁵ | R⁶ | R⁷ | R⁸ |
|---|---|---|---|---|---|
| 4-1 | H | H | H | H | Ph |
| 4-2 | F | H | H | H | H |
| 4-3 | Cl | H | H | H | Ph |
| 4-4 | H | Cl | H | H | Ph |
| 4-5 | Cl | H | Cl | H | H |
| 4-6 | Cl | H | Cl | H | t-Bu |
| 4-7 | Cl | H | Cl | H | Ph |
| 4-8 | Cl | H | Cl | H | SiMe₃ |
| 4-9 | Cl | H | Cl | H | SiEt₃ |
| 4-10 | Cl | H | Cl | H | CH₂SiMe₃ |
| 4-11 | Cl | H | Me | H | t-Bu |
| 4-12 | Cl | H | Me | H | Ph |
| 4-13 | Cl | H | Me | H | SiMe₃ |
| 4-14 | Cl | H | Me | H | SiEt₃ |
| 4-15 | Cl | H | Me | H | CH₂SiMe₃ |
| 4-16 | Me | H | H | H | Ph |
| 4-17 | Me | H | H | H | SiEt₃ |
| 4-18 | Me | H | Cl | H | H |
| 4-19 | Me | H | Cl | H | t-Bu |
| 4-20 | Me | H | Cl | H | Ph |
| 4-21 | Me | H | Cl | H | SiMe₃ |
| 4-22 | Me | H | Cl | H | SiEt₃ |
| 4-23 | Me | H | Cl | H | CH₂SiMe₃ |
| 4-24 | Me | H | Me | H | H |

TABLE 1-continued

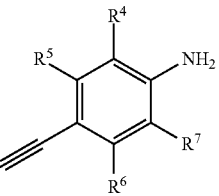

(4)

| Compd. No. | R⁴ | R⁵ | R⁶ | R⁷ | R⁸ |
|---|---|---|---|---|---|
| 4-25 | Me | H | Me | H | t-Bu |
| 4-26 | Me | H | Me | H | Ph |
| 4-27 | Me | H | Me | H | SiMe₃ |
| 4-28 | Me | H | Me | H | CH₂SiMe₃ |
| 4-29 | Me | H | Me | H | SiEt₃ |
| 4-30 | Me | H | H | Me | Ph |
| 4-31 | Me | H | Me | Me | C(Me)₂OH |

TABLE 2

| Compd. No. | R⁴ | R⁵ | R⁶ | R⁷ | R⁸ |
|---|---|---|---|---|---|
| 4-32 | Me | H | F | H | H |
| 4-33 | Me | H | F | H | t-Bu |
| 4-34 | Me | H | F | H | Ph |
| 4-35 | Me | H | F | H | CH₂SiMe₃ |
| 4-36 | Me | H | F | H | SiMe₃ |
| 4-37 | Me | H | F | H | SiEt₃ |
| 4-38 | Me | H | Me | H | C(Me)₂OH |
| 4-39 | Me | H | Me | H | Si(Me)₂(t-Bu) |

TABLE 3

| Compd. No. | ¹H-NMR (CDCl₃/TMS,, δ (ppm)) |
|---|---|
| 4-1 | 3.74(brs, 2H), 6.56(d, 2H), 7.18-7.28(m, 5H), 7.40-7.43(m, 2H) |
| 4-2 | 3.89(brs, 2H), 6.72(t, 1H), 7.12-7.18(m, 2H), 7.30-7.36(m, 3H), 7.48-7.50(m, 2H) |
| 4-3 | 4.21(s, 2H), 6.69(d, 1H), 7.22-7.25(m, 1H), 7.29-7.35(m, 3H), 7.44-7.50(m, 3H) |
| 4-4 | 3.88(brs, 2H), 6.52(4 1H), 6.73(s, 1H), 7.28-7.36(m, 4H), 7.51-7.54(m, 2H) |
| 4-5 | 3.24 (s, 1H), 4.29 (brs, 2H), 6.78 (s, 1H), 7.41 (s, 1H) |
| 4-6 | 1.31 (s, 9H), 4.15 (brs, 2H), 6.75 (s, 1H), 7.30 (s, 1H) |
| 4-7 | 4.27 (brs, 2H), 6.81 (s, 1H), 7.31-7.36 (m, 3H), 7.45 (s, 1H), 7.51-7.53 (m, 2H) |
| 4-8 | 0.25 (s, 9H), 4.25 (brs, 2H), 6.76 (s, 1H), 7.39 (s, 1H) |
| 4-9 | 0.67 (q, 6H), 1.05 (t, 9H), 4.24 (brs, 2H), 6.76 (s, 1H), 7.39 (s, 1H) |
| 4-10 | 0.16 (s, 9H), 1.72 (s, 2H), 4.13 (brs, 2H), 6.75 (s, 1H), 7.28 (s, 1H) |
| 4-11 | 1.30 (s, 9H), 2.28 (s, 3H), 4.01 (s, 2H), 6.57 (s, 1H), 7.25 (s, 1H). |
| 4-12 | 2.40 (s, 3H), 4.13 (brs, 2H), 6.62 (s, 1H), 7.29-7.55 (m, 6H). |
| 4-13 | 0.23 (s, 9H), 2.31 (s, 3H), 4.11 (brs, 2H), 6.56 (s, 1H), 7.32 (s, 1H). |
| 4-14 | 0.66 (q, 6H), 1.38 (t, 9H), 2.33 (s, 3H), 4.10 (s, 2H), 6.57 (s, 1H), 7.34 (s, 1H). |
| 4-15 | 0.15 (s, 9H), 1.71 (s, 2H), 2.29 (s, 3H), 4.00 (brs, 2H), 6.56 (s, 1H), 7.23 (s, 1H). |
| 4-16 | 2.15 (s, 3H), 3.77(brs, 2H), 6.62 (d, 1H), 7.22-7.34(m, 5H), 7.48-7.50(m, 2H) |
| 4-17 | 0.64 (q, 6H), 1.03 (t, 9H), 2,10 (s, 3H), 3.72 (brs, 2H), 6.54 (d, 1H), 7.16 (d, 1H), 7.19 (s, 1H) |
| 4-18 | 2.09 (s, 3H), 3.21 (s, 1H), 3.18 (brs, 2H), 6.67 (s, 1H), 7.20 (s, 1H) |
| 4-19 | 1.32 (s, 9H), 2.07 (s, 3H), 3.69 (brs, 2H), 6.66 (s, 1H), 7.10 (s, 1H) |
| 4-20 | 2.12 (s, 3H), 3.81 (brs, 2H), 6.71 (s, 1H), 7.25 (s, 1H), 7.29-7.35 (m, 3H), 7.51-7.53 (m, 2H) |
| 4-21 | 0.24 (s, 9H), 2.07 (s, 3H), 3.78 (brs, 2H), 6.65 (s, 1H), 7.18 (s, 1H) |
| 4-22 | 0.66 (q, 6H), 1.05 (t, 9H), 2.08 (s, 3H), 3.78 (brs, 2H), 6.66 (s, 1H), 7.18(8, 1H) |
| 4-23 | 0.16 (s, 9H), 1.72 (s, 2H), 2.07 (s, 3H), 3.68 (brs, 2H), 6,65 (s, 1H), 7.09 (s, 1H) |
| 4-24 | 2.10 (s, 3H), 2.34 (s, 3H), 3.13 (s, 1H), 3.69 (brs, 2H), 6.49 (3, 1H), 7.16 (s, 1H) |
| 4-25 | 1.30 (s, 9H), 2.07 (s, 3H), 2.22 (s, 3H), 3.58 (brs, 2H), 6.47 (s, 1H), 7.05 (s, 1H) |
| 4-26 | 2.12 (s, 3H), 2.41(s, 3H), 3.71(brs, 2H), 6.53(s, 1H), 7.28-7.34(m, 3H), 7.48-7.50(m, 2H) |
| 4-27 | 0.23 (s, 9H), 2.08(8, 3H), 2.32(s, 3H), 3.67(s, 2H), 6.47(s, 1H), 7.14(s, 1H) |
| 4-28 | 0.15 (s, 9H), 1.71 (s, 2H), 2.08 (s, 3H), 2.30 (s, 3H), 3.58 (brs, 2H), 6.48 (s, 1H), 7.05 (s, 1H) |
| 4-29 | 0.65 (q, 6H), 1.04 (t, 9H), 2.08 (s, 3H), 2.33 (s, 3H), 3.66 (brs, 2H), 6.47 (s, 1H), 7.14 (s, 1H) |

TABLE 3-continued

| Compd. No. | $^1$H-NMR (CDCl$_3$/TMS,, δ (ppm)) |
|---|---|
| 4-30 | 2.17(s, 6H), 3.74(brs, 2H), 7.16(s, 2H), 7.29-7.34(m, 3H), 7.49(d, 2H) |
| 4-31 | 1.61(s, 6H), 2.09(s, 3H), 2.30(s, 3H), 3.66(s, 2H), 6.49(s, 1H), 7.09(s, 1H) |

TABLE 4

| Compd. No. | $^1$H-NMR (CDCl$_3$/TMS,, δ (ppm)) |
|---|---|
| 4-32 | 2.08 (s, 3H), 3.16 (s, 1H), 3.86 (brs, 2H), 6.49 (d, 1H), 7.13 (d, 1H) |
| 4-33 | 1.31 (s, 9H), 2.06 (s, 3H), 3.74 (brs, 2H), 6.34 (d, 1H), 7.04 (d, 1H) |
| 4-34 | 2.11 (s, 3H), 3.86 (brs, 2H), 6.40 (d, 2H), 7.18 (d, 2H), 7.26-7.37 (m, 3H), 7.49-7.58 (m, 2H) |
| 4-35 | 0.16 (s, 9H), 1.71 (s, 2H), 2.07 (s, 3H), 3.73 (brs, 2H), 6.34 (d, 1H), 7.02 (d, 1H) |
| 4-36 | 0.23 (s, 9H), 3.15 (s, 3H), 3.83 (brs, 2H), 6.32 (d, 1H), 7.10 (d, 1H) |
| 4-37 | 0.65 (q, 6H), 1.04 (t, 9H), 2.07 (s, 3H), 3,82 (brs, 2H), 6.33 (d, 1H), 7.11 (d, 1H) |
| 4-38 | 1.62 (s, 6H), 2.09 (s, 3H), 2.30 (s, 3H), 3.66 (s, 2H), 6.49 (s, 1H), 7.09 (s, 1H) |
| 4-39 | 0.16 (s, 6H), 0.98 (s, 9H), 2.08 (s, 3H), 2.33 (s, 3H), 3.67 (brs, 2H), 6.47 (s, 1H), 7.14 (s, 1H) |

TABLE 5

(1)

| Compd. No. | R$^1$ | R$^2$ | R$^3$ | R$^4$ | R$^5$ | R$^6$ | R$^7$ | R$^8$ |
|---|---|---|---|---|---|---|---|---|
| 1 | Me | H | H | Me | H | H | H | Ph |
| 2 | Et | H | H | Me | H | H | H | Ph |
| 3 | Me | H | H | Me | H | Me | H | SiMe$_3$ |
| 4 | Et | H | H | Me | H | Me | H | SiMe$_3$ |
| 5 | Me | Me | H | H | H | H | H | Ph |
| 6 | Me | Me | H | F | H | H | H | H |
| 7 | Me | Me | H | F | H | H | H | Ph |
| 8 | Me | Me | H | F | H | H | H | Ph-4-t-Bu |
| 9 | Me | Me | H | F | H | H | H | SiMe$_3$ |
| 10 | Me | Me | H | Cl | H | H | H | Ph |
| 11 | Me | Me | H | Cl | H | H | H | SiMe$_3$ |
| 12 | Me | Me | H | H | Cl | H | H | Ph |
| 13 | Me | Me | H | H | Cl | H | H | SiMe$_3$ |
| 14 | Me | Me | H | F | H | H | F | Ph |
| 15 | Me | Me | H | Cl | H | Cl | H | Ph |
| 16 | Me | Me | H | Cl | H | Cl | H | Ph-3-CF$_3$ |
| 17 | Me | Me | H | Cl | H | Me | H | Ph |
| 18 | Me | Me | H | Me | H | H | H | H |
| 19 | Me | Me | H | Me | H | H | H | n-Pr |
| 20 | Me | Me | H | Me | H | H | H | i-Pr |

TABLE 6

| Compd. No. | R$^1$ | R$^2$ | R$^3$ | R$^4$ | R$^5$ | R$^6$ | R$^7$ | R$^8$ |
|---|---|---|---|---|---|---|---|---|
| 21 | Me | Me | H | Me | H | H | H | c-Pr |
| 22 | Me | Me | H | Me | H | H | H | n-Bu |
| 23 | Me | Me | H | Me | H | H | H | t-Bu |
| 24 | Me | Me | H | Me | H | H | H | n-Pen |
| 25 | Me | Me | H | Me | H | H | H | c-Hex |
| 26 | Me | Me | H | Me | H | H | H | CH$_2$(CH$_2$)$_6$CH$_3$ |
| 27 | Me | Me | H | Me | H | H | H | CH$_2$CH$_2$CH$_2$CN |
| 28 | Me | Me | H | Me | H | H | H | CH$_2$OMe |
| 29 | Me | Me | H | Me | H | H | H | CH$_2$Ph |
| 30 | Me | Me | H | Me | H | H | H | CH$_2$CH$_2$Ph |

TABLE 6-continued

| Compd. No. | R$^1$ | R$^2$ | R$^3$ | R$^4$ | R$^5$ | R$^6$ | R$^7$ | R$^8$ |
|---|---|---|---|---|---|---|---|---|
| 31 | Me | Me | H | Me | H | H | H | Ph |
| 32 | Me | Me | SCH$_3$ | Me | H | H | H | Ph |
| 33 | Me | Me | H | Me | H | H | H | Ph-2-F |
| 34 | Me | Me | H | Me | H | H | H | Ph-2-Cl |
| 35 | Me | Me | H | Me | H | H | H | Ph-2-Br |
| 36 | Me | Me | H | Me | H | H | H | Ph-3-F |
| 37 | Me | Me | H | Me | H | H | H | Ph-3-Cl |
| 38 | Me | Me | H | Me | H | H | H | Ph-4-F |
| 39 | Me | Me | H | Me | H | H | H | Ph-4-Cl |
| 40 | Me | Me | H | Me | H | H | H | Ph-3,5-F$_2$ |

TABLE 7

| Compd. No. | R$^1$ | R$^2$ | R$^3$ | R$^4$ | R$^5$ | R$^6$ | R$^7$ | R$^8$ |
|---|---|---|---|---|---|---|---|---|
| 41 | Me | Me | H | Me | H | H | H | Ph-2-Me |
| 42 | Me | Me | H | Me | H | H | H | Ph-2-OMe |
| 43 | Me | Me | H | Me | H | H | H | Ph-3-OMe |
| 44 | Me | Me | H | Me | H | H | H | Ph-4-OMe |
| 45 | Me | Me | H | Me | H | H | H | Ph-2-CF$_3$ |
| 46 | Me | Me | H | Me | H | H | H | Ph-3-CF$_3$ |
| 47 | Me | Me | H | Me | H | H | H | Ph-2-Me-4-OMe |
| 48 | Me | Me | H | Me | H | H | H | Ph-2,4,5-Me$_3$ |
| 49 | Me | Me | H | Me | H | H | H | SiMe$_3$ |
| 50 | Me | Me | H | Me | H | H | H | 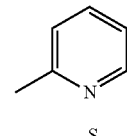 |
| 51 | Me | Me | H | Me | H | H | H | 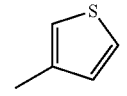 |
| 52 | Me | Me | H | Me | H | Me | H | t-Bu |
| 53 | Me | Me | H | Me | H | Me | H | CH$_2$OMe |
| 54 | Me | Me | H | Me | H | Me | H | CH$_2$OPh |
| 55 | Me | Me | H | Me | H | Me | H | Ph |
| 56 | Me | Me | H | Me | H | Me | H | Ph-4-t-Bu |
| 57 | Me | Me | H | Me | H | Me | H | Ph-3-CF$_3$ |
| 58 | Me | Me | H | Me | H | Me | H | Ph-4-CF$_3$ |
| 59 | Me | Me | H | Me | H | Me | H | SiMe$_3$ |
| 60 | Me | Et | H | F | H | H | H | t-Bu |

TABLE 8

| Compd. No. | R¹ | R² | R³ | R⁴ | R⁵ | R⁶ | R⁷ | R⁸ |
|---|---|---|---|---|---|---|---|---|
| 61 | Me | Et | H | F | H | H | H | Ph |
| 62 | Me | Et | H | F | H | H | H | SiMe₃ |
| 63 | Me | Et | H | Cl | H | H | H | t-Bu |
| 64 | Me | Et | H | Cl | H | H | H | Ph |
| 65 | Me | Et | H | Cl | H | H | H | SiMe₃ |
| 66 | Me | Et | H | Me | H | H | H | t-Bu |
| 67 | Me | Et | H | Me | H | H | H | Ph |
| 68 | Me | Et | H | Me | H | H | H | SiMe₃ |
| 69 | Me | Et | H | Me | H | H | H | SiEt₃ |
| 70 | Me | Et | H | Me | H | H | H | CH₂SiMe₃ |
| 71 | Me | Et | H | CF₃ | H | H | H | t-Bu |
| 72 | Me | Et | H | CF₃ | H | H | H | Ph |
| 73 | Me | Et | H | OCF₃ | H | H | H | t-Bu |
| 74 | Me | Et | H | OCF₃ | H | H | H | Ph |
| 75 | Me | Et | H | OCF₃ | H | H | H | SiMe₃ |
| 76 | Me | Et | H | H | Cl | H | H | Ph |
| 77 | Me | Et | H | H | Cl | H | H | SiMe₃ |
| 78 | Me | Et | H | F | H | F | H | t-Bu |
| 79 | Me | Et | H | F | H | F | H | Ph |
| 80 | Me | Et | H | F | H | F | H | SiMe₃ |

TABLE 9

| Compd. No. | R¹ | R² | R³ | R⁴ | R⁵ | R⁶ | R⁷ | R⁸ |
|---|---|---|---|---|---|---|---|---|
| 81 | Me | Et | H | Cl | H | Cl | H | t-Bu |
| 82 | Me | Et | H | Cl | H | Cl | H | Ph |
| 83 | Me | Et | H | Cl | H | Cl | H | SiMe₃ |
| 84 | Me | Et | H | Cl | H | Me | H | H |
| 85 | Me | Et | H | Cl | H | Me | H | t-Bu |
| 86 | Me | Et | H | Cl | H | Me | H | SiMe₃ |
| 87 | Me | Et | H | Cl | H | Me | H | Ph |
| 88 | Me | Et | H | Cl | H | Me | H | CH₂SiMe₃ |
| 89 | Me | Et | H | Cl | H | Me | H | SiEt₃ |
| 90 | Me | Et | H | Me | H | Cl | H | H |
| 91 | Me | Et | H | Me | H | Cl | H | t-Bu |
| 92 | Me | Et | H | Me | H | Cl | H | Ph |
| 93 | Me | Et | H | Me | H | Cl | H | SiMe₃ |
| 94 | Me | Et | H | Me | H | Cl | H | CH₂SiMe₃ |
| 95 | Me | Et | H | Me | H | Cl | H | SiEt₃ |
| 96 | Me | Et | H | Me | H | Me | H | H |
| 97 | Me | Et | H | Me | H | Me | H | n-Pr |
| 98 | Me | Et | H | Me | H | Me | H | t-Bu |
| 99 | Me | Et | H | Me | H | Me | H | c-Hex |
| 100 | Me | Et | H | Me | H | Me | H | CH₂(CH₂)₆CH₃ |

TABLE 10

| Compd. No. | R¹ | R² | R³ | R⁴ | R⁵ | R⁶ | R⁷ | R⁸ |
|---|---|---|---|---|---|---|---|---|
| 101 | Me | Et | H | Me | H | Me | H | CH₂(CH₂)₇CH₃ |
| 102 | Me | Et | H | Me | H | Me | H | CH₂(CH₂)₁₀CH₃ |
| 103 | Me | Et | H | Me | H | Me | H | CH₂(CH₂)₁₄CH₃ |
| 104 | Me | Et | H | Me | H | Me | H | CH₂CH₂CH₂CN |
| 105 | Me | Et | H | Me | H | Me | H | CH₂OMe |
| 106 | Me | Et | H | Me | H | Me | H | CH₂Ph |
| 107 | Me | Et | H | Me | H | Me | H | CH₂CH₂Ph |
| 108 | Me | Et | H | Me | H | Me | H | —CH₂-phthalimide |
| 109 | Me | Et | H | Me | H | Me | H | —CH₂CH₂-phthalimide |
| 110 | Me | Et | H | Me | H | Me | H | Ph |
| 111 | Me | Et | H | Me | H | Me | H | Ph-2-Cl |
| 112 | Me | Et | H | Me | H | Me | H | Ph-3-Cl |
| 113 | Me | Et | H | Me | H | Me | H | Ph-4-Cl |
| 114 | Me | Et | H | Me | H | Me | H | Ph-4-Me |
| 115 | Me | Et | H | Me | H | Me | H | Ph-4-n-Pr |
| 116 | Me | Et | H | Me | H | Me | H | Ph-4-n-Bu |
| 117 | Me | Et | H | Me | H | Me | H | Ph-4-t-Bu |
| 118 | Me | Et | H | Me | H | Me | H | Ph-2-CF₃ |
| 119 | Me | Et | H | Me | H | Me | H | Ph-3-CF₃ |
| 120 | Me | Et | H | Me | H | Me | H | Ph-4-CF₃ |

TABLE 11

| Compd. No. | R¹ | R² | R³ | R⁴ | R⁵ | R⁶ | R⁷ | R⁸ |
|---|---|---|---|---|---|---|---|---|
| 121 | Me | Et | H | Me | H | Me | H | Ph-4-OMe |
| 122 | Me | Et | H | Me | H | Me | H | Ph-4-OPh |
| 123 | Me | Et | H | Me | H | Me | H | SiMe₃ |
| 124 | Me | Et | H | Me | H | Me | H | SiEt₃ |
| 125 | Me | Et | H | Me | H | Me | H | Si(i-Pr)₃ |
| 126 | Me | Et | H | Me | H | Me | H | Si(Me)₂(t-Bu) |
| 127 | Me | Et | H | Me | H | Me | H | CH₂SiMe₃ |
| 128 | Me | Et | H | Me | H | Me | H | 3-thienyl |
| 129 | Me | Et | H | F | H | H | F | t-Bu |
| 130 | Me | Et | H | F | H | H | F | Ph |
| 131 | Me | Et | H | F | H | H | F | SiMe₃ |
| 132 | Me | i-Pr | H | Me | H | Me | H | SiMe₃ |
| 133 | Me | n-Bu | H | Me | H | H | H | Ph |
| 134 | Me | n-Bu | H | Me | H | Me | H | SiMe₃ |
| 135 | Me | i-Bu | H | Me | H | H | H | Ph |
| 136 | Me | n-Hex | H | Me | H | H | H | Ph |
| 137 | Me | c-Hex | H | Me | H | H | H | CH₂OMe |
| 138 | Me | c-Hex | H | Me | H | H | H | Ph |
| 139 | Me | c-Hex | H | Me | H | H | H | SiMe₃ |
| 140 | Et | Et | H | Me | H | H | H | Ph |

TABLE 12

| Compd. No. | R¹ | R² | R³ | R⁴ | R⁵ | R⁶ | R⁷ | R⁸ |
|---|---|---|---|---|---|---|---|---|
| 141 | Et | Et | H | Me | H | Me | H | SiMe₃ |
| 142 | Et | n-Pr | H | Me | H | H | H | Ph |
| 143 | Et | n-Bu | H | Me | H | H | H | Ph |
| 144 | Et | n-Hex | H | Me | H | H | H | Ph |
| 145 | —CH₂(CH₂)₃CH₂— | | H | Me | H | Me | H | C(Me)₂OH |
| 146 | —CH₂(CH₂)₃CH₂— | | H | Me | H | H | H | Ph |
| 147 | —CH₂(CH₂)₃CH₂— | | H | Me | H | Me | H | SiMe₃ |
| 148 | —C₂H₄—O—C₂H₄— | | H | Me | H | Me | H | SiMe₃ |
| 149 | Me | Et | H | Cl | H | Cl | H | H |
| 150 | Me | Et | H | Cl | H | Cl | H | SiEt₃ |
| 151 | Me | Et | H | Cl | H | Cl | H | CH₂SiMe₃ |
| 152 | Me | Et | H | CF₃ | H | H | H | SiMe₃ |
| 153 | —CH₂(CH₂)₂CH₂— | | H | Me | H | Me | H | SiMe₃ |
| 154 | Me | Et | H | Me | H | F | H | H |
| 155 | Me | Et | H | Me | H | F | H | t-Bu |
| 156 | Me | Et | H | Me | H | F | H | Ph |
| 157 | Me | Et | H | Me | H | F | H | CH₂SiMe₃ |
| 158 | Me | Et | H | Me | H | F | H | SiMe₃ |
| 159 | Me | Et | H | Me | H | F | H | SiEt₃ |
| 160 | Me | Et | H | Me | H | Me | H | C(Me)₂OH |

TABLE 13

| Compd. No. | R¹ | R² | R³ | R⁴ | R⁵ | R⁶ | R⁷ | R⁸ | Form |
|---|---|---|---|---|---|---|---|---|---|
| 161 | Me | Et | H | Me | H | Me | H | C(Me)$_2$OSiMe$_3$ | |
| 162 | Me | Et | H | Me | H | Me | H | SiMe$_3$ | Hydrochloride |
| 163 | Me | Et | H | Me | H | Me | H | Si(Me)$_2$(t-Bu) | Hydrochloride |
| 164 | Me | Me | H | Me | H | Me | H | SiMe$_3$ | Hydrochloride |
| 165 | Me | Me | H | Me | H | Me | H | Si(Me)$_2$(t-Bu) | Hydrochloride |
| 166 | Me | Me | H | Me | H | Cl | H | Ph | |
| 167 | —CH$_2$(CH$_2$)$_3$CH$_2$— | | H | Me | H | Cl | H | Ph-2-Cl | |
| 168 | Me | Et | H | Me | H | Cl | H | Ph-2-Cl | |
| 169 | Me | Me | H | Me | H | Cl | H | Ph-2-Cl | |
| 170 | Me | Et | H | Me | H | Me | H | SiMe$_3$ | p-toluenesulfonate |
| 171 | Me | i-Pr | H | Me | H | Me | H | Si(Me)$_2$(t-Bu) | |
| 172 | Me | Et | H | Me | H | Cl | H | t-Bu | Hydrochloride |
| 173 | Me | Et | H | Me | H | Cl | H | t-Bu | (±)-camphorsulfonate |
| 174 | Me | Et | H | Me | H | Me | H | SiMe$_3$ | (+)-camphorsulfonate |
| 175 | Me | Et | H | Me | H | Me | H | SiMe$_3$ | (−)-camphorsulfonate |
| 176 | Me | Et | H | Me | H | F | H | SiMe$_3$ | Hydrochloride |
| 177 | Me | Et | H | Me | H | F | H | Ph | Hydrochloride |
| 178 | Me | Et | H | Cl | H | Cl | H | SiEt$_3$ | Hydrochloride |
| 179 | —CH$_2$(CH$_2$)$_3$CH$_2$— | | H | Me | H | Me | H | SiMe$_3$ | Hydrochloride |
| 180 | Me | Me | H | Me | H | Cl | H | Ph-2-Cl | |

TABLE 14

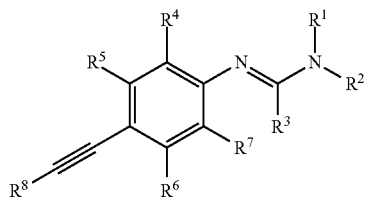

(1)

| Compd. No. | Form | ¹H-NMR (CDCl$_3$/TMS, δ (ppm)) |
|---|---|---|
| 1 | solid | 2.27(s, 3H), 3.01(s, 3H), 4.60(brs, 1H), 6.73(d, 1H), 7.22-7.35(m, 5H), 7.48-7.56(m, 3H) |
| 2 | oil | 1.21(t, 3H), 2.27(s, 3H), 3.01(s, 3H), 3.27-3.33 (m, 2H), 6.72(d, 1H), 7.26-7.35(m, 5H), 7.49-7.51(m, 3H) |
| 3 | solid | 0.23(s, 9H), 2.18(s, 3H), 2.35(s, 3H), 2.99(s, 3H), 6.57(s, 1H), 7.22(s, 1H), 7.26(s, 1H), 7.51(brs, 1H) |
| 4 | solid | 0.24(s, 9H), 1.25(t, 3H), 2.17(s, 3H), 2.36(s, 3H), 3.41(br, 2H), 4.86(br, 1H), 6.58(s, 1H), 7.23(s, 1H), 7.47(brs, 1H) |
| 5 | solid | 3.03(s, 6H), 6.93(d, 1H), 7.29-7.35(m, 3H), 7.43(d, 2H), 7.49-7.52(m, 2H), 7.54(S, 1H) |
| 6 | oil | 3.02(s, 1H), 3.03(s, 6H), 6.84-6.88(m, 1H), 7.14-7.17(m, 2H), 7.58(s, 1H) |

TABLE 14-continued

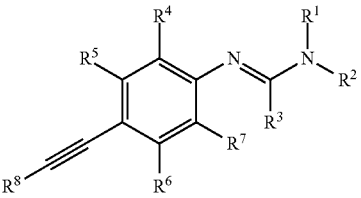

(1)

| Compd. No. | Form | ¹H-NMR (CDCl$_3$/TMS, δ (ppm)) |
|---|---|---|
| 7 | solid | 3.06(s, 6H), 6.90(t, 1H), 7.19-7.23(m, 2H), 7.31-7.35(m, 3H), 7.49-7.51(m, 2H), 7.63(s, 1H) |
| 8 | solid | 1.32(s, 9H), 3.06(s, 6H), 6.90(t, 1H), 7.18-7.22 (m, 2H), 7.35(d, 2H), 7.43(d, 2H), 7.63(s, 1H) |
| 9 | solid | 3.06(s, 6H), 6.85(t, 1H), 7.14-7.18(m, 2H), 7.62(s, 1H) |
| 10 | oil | 3.07(d, 6H), 6.83(d, 1H), 7.30-7.34(m, 4H), 7.49-7.55 (m, 4H) |
| 11 | oil | 0.25(s, 9H), 3.07(d, 1H), 6.79(d, 1H), 7.24-7.27(m, 1H), 7.48(d, 1H), 7.50(S, 1H) |
| 12 | solid | 3.05(s, 6H), 6.85(d, 1H), 7.02(s, 1H), 7.32-7.56(m, 7H) |
| 13 | oil | 3.03(s, 6H), 6.79(d, 1H), 6.97(s, 1H), 7.37(d, 1H), 7.53 (s, 1H) |
| 14 | solid | 3.06(s, 6H), 6.67-6.72(m, 1H), 7.14-7.18(m, 1H), 7.33-7.36(m, 3H), 7.52-7.54(m, 2H), 7.64(s, 1H) |

TABLE 15

| Compd. No. | Form | ¹H-NMR (CDCl$_3$/TMS, δ (ppm)) |
|---|---|---|
| 15 | solid | 3.06(d, 6H), 6.93(s, 1H), 7.33-7.36(m, 3H), 7.49(s, 1H), 7.53-7.55(m, 3H) |
| 16 | oil | 3.09(s, 6H), 6.94(S, 1H), 7.46-7.52(m, 2H), 7.56-7.59(m, 2H), 7.70(d, 1H), 7.79(s, 1H) |
| 17 | oil | 2.43 (s, 3H), 3.07 (brs, 6H), 6.73 (s, 1H), 7.28-7.38 (m, 3H), 7.44-7.56 (m, 4H) |
| 18 | solid | 2.99(s, 1H), 3.02(s, 6H), 6.67(d, 1H), 7.22-7.26(m, 2H), 7.41(s, 1H) |
| 19 | oil | 1.04(1, 3H), 1.59-1.64(m, 2H), 2.22(s, 3H), 2.37(t, 2H), 6.65(d, 1H), 7.13(d, 1H), 7.19(s, 1H), 7.40(s, 1H) |
| 20 | oil | 0.94(d, 6H), 1.49(q, 2H), 1.72-1.77(m, 1H), 2.22(s, 3H), 2.39(t, 2H), 3.01(s, 6H), 6.64(d, 1H), 7.12(d, 1H), 7.18(s, 1H), 7.39(s, 1H) |
| 21 | oil | 0.77-0.85(m, 4H), 1.41-1.45(m, 1H), 2.21(s, 3H), 3.00(s, 6H), 6.63(d, 1H), 7.11 (d, 1H), 7.17(s, 1H), 7.39(s, 1H) |
| 22 | oil | 0.94(t, 3H), 1.44-1.50(m, 2H), 1.54-1.59(m, 2H), 2.22(s, 3H), 2.39(t, 2H), 3.01(s, 6H), 6.65(d, 1H), 7.13(d, 1H), 7.19(s, 1H), 7.40(s, 1H) |
| 23 | oil | 1.30(s, 9H), 2.22(s, 3H), 3.01(s, 6H), 6.64(d, 1H), 7.12(d, 1H), 7.18(s, 1H), 7.44(s, 1H) |
| 24 | oil | 0.91(t, 3H), 1.32-1.45(m, 4H), 1.57-1.61 (m, 2H, 2.22(s, 3H), 2.37(t, 2H), 2.99(s, 6H), 6.64(d, 1H), 7.13(d, 1H), 7.19(s, 1H), 7.38(s, 1H) |

TABLE 15-continued

| Compd. No. | Form | ¹H-NMR (CDCl₃/TMS, δ (ppm)) |
|---|---|---|
| 25 | oil | 1.30-1.34(m, 3H), 1.48-1.56(m, 3H), 1.72-1.77(m, 2H), 1.84-1.88(m, 2H), 2.22(s, 3H), 2.55-2,57(m, 1H), 3.00(s, 6H), 6.64(d, 1H), 7.13(d, 1H), 7.19(s, 1H), 7.26(s, 1H) |
| 26 | oil | 0.88(t, 3H), 1.26-1.33(m, 8H), 1.42-1.45(m, 2H), 1.58(t, 2H), 2.22(s, 3H), 2.38(t, 2H), 3.01(s, 6H), 6.64(d, 1H), 7.13(d, 1H), 7.19(s, 1H), 7.40(s, 1H) |
| 27 | oil | 1.92(q, 2H), 2.23(s, 3H), 2.52-2.58(m, 4H), 3.00(s, 6H), 6.65(d, 1H), 7.13(d, 1H), 7.18(s, 1H), 7.39(s, 1H) |
| 28 | oil | 2.23(s, 3H), 3.02(s, 6H), 3.44(s, 3H), 4.31(s, 2H), 6.67(d, 1H), 7.19(d, 1H), 7.25(d, 1H), 7.41(s, 1H) |
| 29 | oil | 2.24(s, 3H), 3.00(s, 6H), 3.82(s, 2H), 6.66(d, 1H), 7.18-7.25(m, 3H), 7.32(t, 2H), 7.41 (t, 3H) |
| 30 | oil | 2.23(s, 3H), 2.67(t, 2H), 2.91(t, 2H), 3.00(s, 6H), 6.64 (d, 1H), 7.12(d, 1H), 7.18-7.33(m, 6H), 7.39(s, 1H) |

TABLE 16

| Compd. No. | Form | ¹H-NMR (CDCl₃/TMS, δ (ppm)) |
|---|---|---|
| 31 | oil | 2.19(s, 3H), 2.94(s, 6H), 6.63(d, 1H), 7.17-7.26(m, 5H), 7.35(s, 1H), 7.41-7.43(m, 2H) |
| 32 | oil | 1.99(s, 3H), 2.61(s, 3H), 3.11(s, 6H), 6.78(d, 1H), 7.26-7.35(m, 5H), 7.49-7.51(m, 2H) |
| 33 | oil | 2.27(s, 3H), 3.01(s, 6H), 6.71(d, 1H), 7.05-7.11(m, 2H), 7.27-7.31(m, 2H), 7.13(d, 1H), 7.35(s, 1H), 7.46-7.50(m, 1H) |
| 34 | oil | 2.27(s, 3H), 3.03(s, 6H), 6.72(d, 1H), 7.20-7.23(m, 2H), 7.31(s, 1H), 7.37-7.44(m, 3H), 7.52(d, 1H) |
| 35 | oil | 2.27(s, 3H), 3.01(s, 6H), 6.71(d, 1H), 7.12(t, 1H), 7.25(t, 1H), 7.32(d, 1H), 7.39(d, 2H), 7.51(d, 1H), 7.58(d, 1H) |
| 36 | oil | 2.27(s, 3H), 3.03(s, 6H), 6.72(d, 1H), 6.98-7.01(m, 1H), 7.18(d, 1H), 7.26-7.29(m, 3H), 7.32(s, 1H), 7.44(s, 1H) |
| 37 | oil | 2.27(s, 3H), 3.02(s, 6H), 6.71(d, 1H), 7.24-7.28(m, 3H), 7.32(s, 1H), 7.35-7.38(m, 1H), 7.43(s, 1H), 7.49(s, 1H) |
| 38 | oil | 2.27(s, 3H), 3.00(s, 6H), 6.70(d, 1H), 6.98-7.03(m, 2H), 7.25(d, 1H), 7.32(s, 1H), 7.41(s, 1H), 7.45-7.48(m, 2H) |
| 39 | solid | 2.26(s, 3H), 3.02(s, 6H), 6.70(d, 1H), 7.25-7.32(m, 4H), 7.40-7.43(m, 3H) |
| 40 | oil | 2.27(s, 3H), 3.02(s, 6H), 6.70-6.77(m, 2H), 6.98-7.02(m, 2H), 7.25-7.27(m, 1H), 7.32(s, 1H), 7.42(s, 1H) |
| 41 | oil | 2.27(s, 3H), 2.50(s, 3H), 2.97(s, 6H), 6.69(d, 1H), 7.10-7.21(d, 1H), 7.27(d, 1H), 7.33(s, 1H), 7.38(s, 1H), 7.45(s, 1H) |
| 42 | oil | 2.26(s, 3H), 3.01(s, 6H), 3.90(s, 3H), 6.70(d, 1H), 6.87-6.94(m, 2H), 7.24-7.31(m, 2H), 7.36(s, 1H), 7.61(s, 1H), 7.47(d, 1H) |
| 43 | solid | 2.26(s, 3H), 2.34(s, 3H), 3.01(s, 6H), 6.70(d, 1H), 7.09(d, 1H), 7.19-7.33(m, 5H), 7.42(s, 1H) |
| 44 | solid | 2,26(s, 3H), 2.36(s, 3H), 3.03(s, 6H), 6.71(d, 1H), 7.13(d, 2H), 7.27(d, 1H), 7.39-7.43(m, 3H) |
| 45 | oil | 2.27(s, 3H), 3.03(s, 6H), 6.72(d, 4H), 7.30(d, 1H), 7.36(t, 2H), 7.44(s, 1H), 7.49(t, 1H), 7.62-7.66(m, 2H) |
| 46 | oil | 2.28(s, 3H), 3.04(s, 6H), 6.73(d, 1H), 7.26-7.30(m, 1H), 7.34(s, 1H), 7.42-7.46(m, 2H), 7.53(d, 1H), 7.65(d, 1H), 7.76(s, 1H) |

TABLE 17

| Compd. No. | Form | ¹H-NMR (CDCl₃/TMS, δ (ppm)) |
|---|---|---|
| 47 | solid | 2.27(s, 3H), 2.49(s, 3H), 3.03(s, 6H), 3.81(s, 3H), 6.68-6.72(m, 2H), 6.76(s, 1H), 7.24-7.26(m, 2H), 7.31(s, 1H), 7.39(d, 1H), 7.43(s, 1H) |
| 48 | solid | 2.21(d, 6H), 2.27(s, 3H), 2.43(s, 3H), 3.01(s, 6H), 6.70(d, 1H), 6.97(s, 1H), 7.23-7.27(m, 2H), 7.31(s, 1H), 7.41(s, 1H) |
| 49 | oil | 0.21(s, 9H), 2.22(t, 3H), 2.98(s, 6H), 6.53(d, 1H), 7.18(d, 1H), 7.24(s, 1H), 7.36(s, 1H) |
| 50 | oil | 2.26(s, 3H), 3.02(5, 6H), 6.71(d, 1H). 7.17-7.21(m, 1H), 7.34(d, 1H), 7.40(s, 1H), 7.44(s, 1H), 7.48(d, 1H), 7.62-7.67(m, 1H), 8.59(s, 1H) |
| 51 | oil | 2.26(s, 3H), 2.97(s, 6H), 6.68(d, 1H), 7.15(d, 1H), 7.24(d, 2H), 7.31(s, 1H), 7.37(s, 1H), 7.43(s, 1H) |
| 52 | oil | 1.31 (s, 9H), 2.17 (s, 3H), 2.32 (s, 3H), 3.00 (s, 6H), 6.55 (s, 1H), 7.13(s, 1H), 7.38 (s, 1H) |
| 53 | solid | 2.19(s, 3H), 2.36(s, 3H), 3.01(s, 6H), 3.46(s, 3H), 4.36(s, 2H), 6.57(s, 1H), 7.20(s, 1H), 7.40(s, 1H) |

TABLE 17-continued

| Compd. No. | Form | $^1$H-NMR (CDCl$_3$/TMS, δ (ppm)) |
| --- | --- | --- |
| 54 | oil | 2.18(s, 3H), 2.30(s, 3H), 3.01(s, 6H), 4.95(s, 2H), 6.54(s, 1H), 6.98(t, 1H), 7.04-7.06(m, 2H), 7.18(s, 1H), 7.31(t, 2H), 7.39(s, 1H) |
| 55 | solid | 2.23(s, 3H), 2.44(s, 3H), 3.02(s, 6H), 6.61(s, 1H), 7.29-7.35(m, 4H), 7.43(s, 1H), 7.50-7.52(m, 2H) |
| 56 | solid | 1.31(s, 9H), 2.22(s, 3H), 2.43(s, 3H), 3.00(s, 6H), 6.60(s, 1H), 7.28(s, 1H), 7.33-7.45(m, 5H) |
| 57 | oil | 2.23(s, 3H), 2.44(s, 3H), 3.03(s, 6H), 6.62(s, 1H), 7.29(s, 1H), 7.43-7.46(s, 2H), 7.53(d, 1H), 7.65(d, 1H), 7.75(s, 1H) |
| 58 | oil | 2.23(s, 3H), 2.44(s, 3H), 3.03(s, 6H), 6.62(s, 1H), 7.30(s, 1H), 7.44(s, 21H), 7.58(s, 4H) |
| 59 | amorphous | 0.24(s, 9H), 2.18(s, 3H), 2.35(s, 3H), 3.01(s, 6H), 6.55(s, 1H), 7.22(s, 1H), 7.40(s, 1H) |
| 60 | oil | 1.21(t, 3H), 1.29(s, 9H), 3.01(s, 3H), 3.28-3.53(m, 2H), 6.82(t, 1H), 7.02-7.06(m, 2H), 7.51-7.63(m, 1H) |
| 61 | oil | 1.21(t, 3H), 3.03(s, 3H), 3.28-3.56(m, 2H), 6.90(t, 1H), 7.18-7.25(m, 2H), 7.28-7.3 8(m, 3H), 7.48-7.53 ms, 2H), 7.67(s, 1H) |
| 62 | oil | 0.24(s, 9H), 1.24(t, 3H), 3.05(s, 3H), 3.32-3.57(m, 2H), 6.87(t, 1H), 7.14-7.17(m, 2H), 7.67(s, 1H) |

TABLE 18

| Compd. No. | Form | $^1$H-NMR (CDCl$_3$/TMS, δ (ppm)) |
| --- | --- | --- |
| 63 | oil | 1.22(t, 3H), 1.30(s, 9H), 3.03(s, 3H), 3.29-3.53(m, 2H), 6.76(d, 1H), 7.15(d, 1H), 7.50-7.69(m, 2H) |
| 64 | oil | 1.20(t, 3H), 2.98(d, 3H), 3.27-3.54(m, 2H), 6.82(d, 1H), 7.27-7.33(m, 4H), 7.38-7.54(m, 4H) |
| 65 | oil | 0.21(s, 9H), 1.20(t, 3H), 2.78(d, 3H), 3.07-3.30(m, 2H), 6.55(s, 1H), 7.00(d, 1H), 7.23(s, 1H), 7.25(d, 1H) |
| 66 | oil | 1.20(t, 3H), 1.30(s, 9H), 2.22(s, 3H), 2.99(s, 3H), 3.32(brs, 2H), 6.64(d, 1H), 7.12(d, 1H), 7.18(s, 1H), 7.41(brs, 1H) |
| 67 | oil | 1.22(t, 3H), 2.27(s, 3H), 3.01(s, 3H), 3.33(brs, 2H), 6.72(d, 1H), 7.26-7.35(m, 5H), 7.45-7.52(m, 3H) |
| 68 | oil | 0.23(s, 9H), 1.21(t, 3H), 2.22(s, 3H), 3.00(s, 3H), 3.31(brs, 2H), 6.66(d, 1H), 7.21(d, 1H), 7.26(s, 1H), 7.51(brs, 1H) |
| 69 | oil | 0.65 (q, 6H), 1.03 (t, 9H), 1.20 (s, 3H), 2.22 (s, 3H), 3.00 (s, 3H), 3.41 (brs, 2H), 6.65 (d, 1H), 7.21 (d, 1H), 7.26 (s, 1H), 7.44 (brs, 1H) |
| 70 | oil | 0.15 (s, 9H), 1.19 (t, 3H), 1.68 (s, 2H), 2.22 (s, 3H), 2.99 (s, 3H), 3.33 (brs, 2H), 6.63 (d, 1H), 7.10 (d, 1H), 7.15 (s, 1H), 7.39(brs, 1H) |
| 71 | oil | 1.12(t, 3H), 1.23(s, 9H), 2.92(s, 3H), 3.31(d, 2H), 6.71 (s, 1H), 7.30(d, 1H), 7.36(d, 1H), 7.51(5, 1H) |
| 72 | oil | 1.13(t, 3H), 2.92(d, 3H), 3.21-3.44(m, 2H), 6.77(d, 1H), 7.22-7.27(m, 3H), 7.41-7.45(m, 4H), 7.66(d, 1H) |
| 73 | oil | 1.20(t, 3H), 1.30(s, 9H), 3.01(s, 3H), 3.29-3.51(m, 2H), 6.83(d, 1H), 7.18-7.22(m, 2H), 7.41-7.52(m, 1H) |
| 74 | oil | 1.20(t, 3H), 3.01(d, 3H), 3.45-3.53(m, 2H), 6.90(d, 1H), 7.31-7.38(m, 4H), 7.49-7.57(m, 3H) |
| 75 | oil | 0.26(s, 9H), 1.22(t, 3H), 3.03(s, 3H), 3.31-3.54(m, 2H), 6.87(d, 1H), 7.28-7.35(m, 2H), 7.44-7.56(m, 3H) |
| 76 | oil | 1.21(t, 3H), 3.00(s, 3H), 2.28-3.47(m, 2H), 6.83(d, 1H), 7.02(s, 1H), 7.29-7.34(m, 3H), 7.41(d, 1H), 7.52-7.58(m, 3H) |
| 77 | oil | 0.26(s, 9H), 1.22(t, 3H), 3.00(s, 3H), 3.30-3.50(m, 2H), 6.78(d, 1H), 6.96(s, 1H), 7.36(d, 1H), 7.47-7.57(m, 1H) |
| 78 | oil | 1.11-1.30 (m, 3H), 1.34 (s, 9H), 3.00 (s, 3H), 3,38-3.56 (m, 2H), 6.40-6.52 (m, 2H), 7.40-7.60 (m, 1H). |

TABLE 19

| Compd. No. | Form | $^1$H-NMR (CDCl$_3$/TMS, δ (ppm)) |
| --- | --- | --- |
| 79 | oil | 1.22(t, 3H), 3.03(d, 3H), 3.29-3.55(m, 2H), 6.67-6.71(m, 1H), 7.13-7.17(m, 1H), 7.33-7.36(m, 3H), 7.50-7.66(m, 3H) |
| 80 | oil | 0.26 (s, 9H), 1.11-1.30 (m, 3H), 3.00 (s, 3H), 3.25-3.56 (m, 2H), 6.41-6.53 (m, 2H), 7.45-7.61 (m, 1H). |
| 81 | oil | 1.17-1.30 (m, 3H), 1.33 (s, 9H), 2.99-3.09 (m, 3H), 3.29-3.60 (m, 2H), 6.83-6.91 (m, 1H), 7.36-7.56 (m, 2H). |
| 82 | oil | 1.18-1.33 (m, 3H), 2.98-3.11 (m, 3H), 3.29-3.62 (m, 2H), 6.91-7.00 (m, 1H), 7.30-7.61 (m, 7H). |

TABLE 19-continued

| Compd. No. | Form | ¹H-NMR (CDCl₃/TMS, δ (ppm)) |
|---|---|---|
| 83 | oil | 0.26 (s, 9H), 1.19-1.30 (m, 3H), 3.00-3.07 (m, 3H), 3.28-3.59 (m, 2H), 6.86-6.91 (m, 1H), 7.40-7.57 (m, 2H). |
| 84 | oil | 1.23 (t, 3H), 2.37 (s, 3H), 3.05 (s, 3H), 3.23 (s, 1H), 3.29-3.61 (m, 2H), 6.71 (s, 1H), 7.35-7.60 (m, 2H) |
| 85 | oil | 1.22 (t, 3H), 1.31 (s, 9H), 2.32 (s, 3H), 3.03 (brs, 3H), 3.25-3.61 (m, 2H), 6.78 (s, 1H), 7.32-7.58 (m, 2H) |
| 86 | oil | 0.24 (s, 9H), 1.23 (t, 3H), 2.35 (s, 3H), 3.04 (s, 3H), 3.25-3.60 (m, 2H), 6.68 (s, 1H), 7.30-7.60 (m, 2H) |
| 87 | oil | 1.24 (t, 3H), 2.44 (s, 3H), 3.06 (s, 3H), 3.28-3.64 (m, 2H), 6.74 (s, 1H), 7.28-7.63 (m, 7H) |
| 88 | oil | 0.16 (s, 9H), 1.22 (t, 3H), 1.73 (s, 2H), 2.32 (s, 3H), 3.03 (s, 3H), 3.25-3.63 (m, 2H), 6.67 (s, 1H), 7.33 (s, 1H), 7.35-7.59 (m, 1H) |
| 89 | oil | 0.67 (q, 6H), 1.05 (t, 9H), 1.23 (t, 3H), 2.36 (s, 3H), 3.04 (s, 3H), 3.25-3.65 (m, 2H), 6.69 (s, 1H), 7.33-7.59 (m, 2H) |
| 90 | oil | 1.22 (t, 3H), 2.19 (s, 3H), 3.00 (s, 3H), 3.27 (s, 1H), 3.41 (brs, 2H), 6.76 (s, 1H), 7.28 (s, 1H), 7.42 (brs, 1H) |
| 91 | oil | 1.19 (t, 3H), 1.33 (s, 9H), 2.17 (s, 3H), 2.99 (s, 3H), 3.32 (brs, 2H), 6.75 (s, 1H), 7.18 (s, 1H), 7.41 (brs, 1H) |
| 92 | oil | 1.22 (t, 3H), 2.22 (s, 3H), 3.01 (s, 3H), 3.41 (brs, 2H), 6.80 (s, 1H), 7.25-7.36 (m, 4H), 7.49 (brs, 1H), 7.51-7.55 (m, 2H) |
| 93 | oil | 0.25 (s, 9H), 1.21 (t, 3H), 1.58 (s, 3H), 3.00 (s, 3H), 3.41 (brs, 2H), 6.75 (s, 1H), 7.26 (s, 1H), 7.41 (brs, 1H) |
| 94 | oil | 0.17 (s, 9H), 1.20 (t, 3H), 1.74 (s, 2H), 2.17 (s, 3H), 2.99 (s, 3H), 3.39 (brs, 2H), 6.74 (s, 1H), 7.17 (s, 1H), 7.40 (brs, 1H) |

TABLE 20

| Compd. No. | Form | ¹H-NMR (CDCl₃/TMS, δ (ppm)) |
|---|---|---|
| 95 | oil | 0.67 (q, 6H), 1.06 (t, 9H), 1.20 (t, 3H), 2.18 (s, 3H), 2.99 (s, 3H), 3.40 (brs, 2H), 6.75 (s, 1H), 7.25 (s, 1H), 7.45 (brs, 1H) |
| 96 | oil | 1.21 (t, 3H), 2.19 (s, 3H), 2.37 (s, 3H), 2.99 (s, 3H), 3.19 (s, 1H), 3.21-3.56 (m, 2H), 6.57 (s, 1H), 7.24 (s, 1H), 7.42 (brs, 1H). |
| 97 | oil | 1.05 (t, 3H), 1.93 (t, 3H), 1.60-1.65 (m, 2H), 2.18 (s, 3H), 2.34 (s, 3H), 2.41 (t, 2H), 2.98 (s, 3H), 3.32 (brs, 2H), 6.55 (s, 1H), 7.15 (s, 1H), 7.53 (brs, 1H) |
| 98 | oil | 1.91 (t, 3H), 1.32 (s, 9H), 2.18 (s, 3H), 2.32 (s, 3H), 2.97 (s, 3H), 3.30 (brs, 2H), 6.55 (s, 1H), 7.13 (s, 1H), 7.39 (brs, 1H) |
| 99 | oil | 1.27 (t, 3H), 1.33-1.37 (m, 3H), 1.50-1.59 (m, 3H), 1.75-1.80 (m, 2H), 1.85-1.88 (m, 2H), 2.18 (s, 3H), 2.34 (s, 3H), 2.61-2.65 (m, 1H), 2.99 (s, 3H), 3.53 (brs, 2H), 6.55 (s, 1H), 7.15 (s, 1H), 7.40 (brs, 1H) |
| 100 | oil | 0.88 (t, 3H), 1.21 (t, 3H), 1.26-1.30 (m, 8H), 1.44-1.47 (m, 2H), 1.58 (t, 2H), 2.18 (s, 3H), 2.34 (s, 3H), 2.42 (t, 2H), 3.32 (brs, 2H), 6.55 (s, 1H), 7.15 (s, 1H), 7.41 (brs, 1H) |
| 101 | oil | 0.88 (t, 3H), 1.18 (t, 3H), 1.28-1.33 (m, 10H), 1.46 (t, 2H), 1.56-1.61 (m, 2H), 2.18 (s, 3H), 2.34 (5, 3H), 2.43 (q, 2H), 2.97 (s, 3H), 3.32 (brs, 2H), 6.55 (s, 1H), 7.14 (s, 1H), 7.40 (brs, 1H) |
| 102 | oil | 0.88 (t, 3H), 1.21 (t, 3H), 1.19-1.26 (m, 14H), 1.45 (t, 2H), 1.56-1.65 (m, 4H), 2.18 (s, 3H), 2.34 (s, 3H), 2.42 (t, 3H), 2.98 (s, 3H), 3.31 (brs, 2H), 6.55 (s, 1H), 7.14 (s, 1H), 7.41 (brs, 1H) |
| 103 | oil | 0.88 (m, 4H), 1.19 (t, 3H), 1.17-1.29 (m, 25H), 1.45 (t, 2H), 1.51-1.65 (m, 2H), 2.18 (s, 3H), 2.33 (s, 3H), 2.42 (t, 2H), 2.98 (s, 3H), 3.31 (brs, 2H), 6.55 (s, 1H), 7.14 (s, 1H), 7.41 (brs, 1H) |
| 104 | oil | 1.20 (t, 3H), 1.96 (q, 2H), 2.20 (s, 3H), 2.33 (s, 3H), 2.50-2.64 (m, 4H), 2.99 (s, 3H), 3.33 (brs, 2H), 6.56 (s, 1H), 7.14 (s, 1H), 7.42 (brs, 1H) |
| 105 | oil | 1.20 (t, 3H), 2.19 (s, 3H), 2.36 (s, 3H), 2.99 (s, 3H), 3.34 (brs, 2H), 3.42 (s, 3H), 4.36 (s, 2H), 6.57 (s, 1H), 7.20 (s, 1H), 7.43 (brs, 1H) |
| 106 | oil | 1.19 (t, 3H), 2.19 (q, 3H), 2.37 (s, 3H), 2.98 (s, 3H), 3.31 (brs, 3H), 3.87 (s, 2H), 6.57 (s, 1H), 7.23-7.26 (m, 2H), 7.32 (t, 2H), 7.42-744 (m, 3H) |
| 107 | oil | 1.19 (t, 3H), 2.18 (s, 3H), 2.27 (s, 3H), 2.73 (t, 2H), 2.93 (t, 2H), 2.99 (s, 3H), 3.31 (brs, 2H), 6.54 (s, 1H), 7.13 (s, 1H), 7.19-7.32 (m, 5H), 7.40 (brs, 1H) |
| 108 | amorphous | 1.19 (t, 3H), 2.15 (s, 3H), 2.32 (s, 3H), 2.98 (s, 3H), 3.32 (brs, 1H), 4.70 (s, 2H), 6.53 (s, 1H), 7.16 (s, 1H), 7.40 (brs, 1H), 7.71-7.75 (m, 1H), 7.86-7.91 (m, 2H) |

TABLE 21

| Compd. No. | Form | ¹H-NMR (CDCl₃/TMS, δ (ppm)) |
|---|---|---|
| 109 | solid | 1.18(t, 3H), 2.15(s, 3H), 2.24(s, 3H), 2.87(t, 2H), 2.98(s, 3H), 3.32(brs, 2H), 3.96(t, 2H), 6.50(s, 1H), 7.06(s, 1H), 7.38(brs, 1H), 7.70-7.73(m, 2H), 7.83-7.88(m, 2H) |
| 110 | oil | 1.21(t, 3H), 2.22(s, 3H), 2.44(s, 3H), 3.00(s, 3H), 3.31(brs, 2H), 6.61(d, 1H), 7.25-7.35(m, 4H), 7.42-7.52(m, 3H) |
| 111 | oil | 1.20(t, 3H), 2.23(s, 3H), 2.48(s, 3H), 2.99(s, 3H), 3.31(brs, 2H), 6.61(s, 1H), 7.19-7.22(m, 2H), 7.32(s, 1H), 7.39-7.42(m, 2H), 7.52-7.54(m, 1H) |
| 112 | oil | 1.21(t, 3H), 2.22(s, 3H), 2.43(s, 3H), 3.00(s, 3H), 3.32(brs, 2H), 6.61(s, 1H), 7.22-7.27(m, 3H), 7.34-7.39(m, 3H) |
| 113 | solid | 1.20(t, 3H), 2.22(s, 3H), 2.42(s, 3H), 2.99(s, 3H), 3.31(brs, 2H), 6.60(s, 1H), 7.27-7.30(m, 3H), 7.38-7.43(m, 3H) |
| 114 | oil | 1.20(t, 3H), 2.22(s, 3H), 2.35(s, 3H), 2.45(s, 3H), 2.98(s, 3H), 3.32(brs, 2H), 6.60(s, 1H), 7.12(d, 2H), 7.27(s, 1H), 7.38-7.43(m, 3H) |
| 115 | oil | 0.93(t, 3H), 1.19(q, 3H), 1.63(q, 2H), 2.22(s, 3H), 2.43(s, 3H), 2.57(t, 2H), 2.98(s, 3H), 3.31(brs, 2H), 6.60(s, 1H), 7.12(d, 2H), 7.27(s, 1H), 7.41(d, 3H) |
| 116 | oil | 0.92(t, 3H), 1.21(t, 3H), 1.35(q, 2H), 1.60(q, 2H), 2.22(s, 3H), 2.43(s, H), 2.60(t, 2H), 2.99(s, 3H), 3.33(brs, 2H), 6.60(s, 1H), 7.13(d, 2H), 7.27(s, 1H), 7.41(d, 3H) |
| 117 | solid | 1.21(t, 3H), 1.32(s, 9H), 2.22(s, 3H), 2.43(s, 3H), 3.00(s, 3H), 3.33(brs, 2H), 6.60(s, 1H), 7.28(s, 1H), 7.35(d, 2H), 7.44(d, 3H) |
| 118 | oil | 1.21(t, 3H), 2.23(s, 3H), 2.45(s, 3H), 2.98(s, 3H), 3.29(brs, 2H), 6.61(s, 1H), 7.30-7.35(m, 2H), 7,45-7.53(m, 2H), 7.63(t, 2H) |
| 119 | oil | 1.21(t, 3H), 2.24(s, 3H), 2.45(s, 3H), 3.06(s, 3H), 3.33(brs, 2H), 6.62(s, 1H), 7.29(s, 1H), 7.42-7.46(m, 2H), 7.52(d, 1H), 7.65(d, 1H), 7.75(s, 1H) |
| 120 | oil | 1.21(t, 3H), 2.23(s, 3H), 2.44(s, 3H), 3.01 (s, 3H), 3.31(brs, 2H), 6.62(s, 1H), 7.30(s, 1H), 7.48(s, 1H), 7.58(s, 4H) |
| 121 | solid | 1.20(t 3H), 2.22(s, 3H), 2.42(s, 3H), 2.99(s, 3H), 3.31(brs, 2H), 3.81(s, 3H), 6.60(s, 1H), 6.86(d, 2H), 7.25(s, 1H), 7.42-7.46(m, 3H) |
| 122 | oil | 0.93(t, 3H), 1.19-1.28(m, 3H), 1.37-1.44(m, 14H), 1.78(t, 2H), 2.04(s, 3H), 2.42(s, 3H), 3.00(s, 3H), 3.32(brs, 2H), 3.96(t, 2H), 6.60(s, 1H), 6.85(d, 2H), 7.26(s, 1H), 7.41-7.44(m, 3H) |

TABLE 22

| Compd. No. | Form | ¹H-NMR (CDCl₃/TMS, δ (ppm)) |
|---|---|---|
| 123 | solid | 0.24(s, 9H), 1.20(t, 3H), 2.18(s, 3H), 2.36(s, 3H), 2.99(s, 3H), 3.32-3.51(m, 2H), 6.56(s, 1H), 7.22(s, 1H), 7.45(brs, 1H) |
| 124 | oil | 0.67(q, 6H), 1.06(t, 9H), 1.20(t, 3H), 2.18(s, 3H), 2.37(s, 3H), 3.00(s, 3H), 3.32(brs, 2H), 6.56(s, 1H), 7.23(s, 1H), 7.41(brs, 1H) |
| 125 | oil | 1.13(s, 21H), 1.20(t, 3H), 2.04(s, 3H), 2.19(s, 3H), 2.38(s, 3H), 3.00(s, 3H), 3.34(brs, 2H), 6.56(s, 1H), 7.23(s, 1H), 7.40(brs, 1H) |
| 126 | oil | 0.21(s, 6H), 1.02(t, 9H), 1.22(t, 3H), 2.21 (s, 3H), 2.29(s, 3H), 3.01 (s, 3H), 3.24(brs, 2H), 6.58(s, 1H), 7.25(s, 1H), 7.42(brs, 1H) |
| 127 | oil | 0.12(s, 9H), 1.13(t, 3H), 1.67(s, 2H), 2.12(s, 3H), 2.28(s, 3H), 2.91 (s, 3H), 3.27(s, 2H), 6.49(s, 1H), 7.07(s, 1H), 7.34(s, 1H) |
| 128 | oil | 1.22(t, 3H), 2.21(s, 3H), 2.42(s, 3H), 3.00(s, 3H), 3.32(brs, 2H), 6.60(s, 1H), 7.17(d, 1H), 7.25-7.28(m, 2H), 7.44-7.45(m, 2H) |
| 129 | oil | 1.21(t, 3H), 1.29(s, 9H), 3.02(d, 3H), 3.33(d, 2H), 6.85-6.92(m, 2H), 7.73(s, 1H) |
| 130 | oil | 1.21(t, 3H), 3.01(d, 3H), 3.26-3.57(m, 2H), 7.01-7.05(m, 2H), 7.31-7.33(m, 3H), 7.47-7.50(m, 2H), 7.63-7.76(m, 1H) |
| 131 | oil | 0.24(s, 9H), 1.24(t, 3H), 3.02-3.07(m, 3H), 3.30-3.60(m, 2H), 6.98(d, 2H), 7.78(s, 1H) |
| 132 | solid | 0.24 (s, 9H), 1.24 (d, 6H), 2.18 (s, 3H), 2.35 (s, 3H), 2.90 (s, 3H), 3.54-3.79 (m, 1H), 6.56 (s, 1H), 7.21 (s, 1H), 7.50 (brs, 1H). |
| 133 | oil | 0.95(t, 3H), 1.33(brs, 2H), 1.56(brs, 3H), 2,26(s, 3H), 2.99(s, 3H), 3.21-3.46(m, 2H), 6.70(d, 1H), 7.26-7.33(m, 5H), 7.43(s, 1H), 7.49-7.51(m, 2H) |
| 134 | oil | 0.24 (s, 9H), 0.96 (t, 3H), 1.30-1.42 (m, 2H), 1.54-1.70 (m, 2H), 2.18 (s, 3H), 2,35 (s, 3H), 2.99 (s, 3H), 3.19-3.53 (m, 2H), 6.54 (s, 1H), 7.21 (s, 1H), 7.41(s, 1H) |
| 135 | oil | 0.90(s, 6H), 2.01-2.03(m, 1H), 2.26(s, 3H), 2.99(s, 3H), 6.69(d, 1H), 7.27-7.33(m, 5H), 7.49(s, 1H), 7.48-7.51(m, 2H) |
| 136 | oil | 0.89(t, 3H), 1.26(brs, 6H), 1.59(brs, 2H), 2.26(s, 3H), 3.00(s, 3H), 3.23-3.51(m, 2H), 6.71(d, 1H), 7.26-7.35(m, 6H), 7.45(brs, 1H), 7.49-7.52(m, 2H) |
| 137 | oil | 1.09-1.16(m, 1H), 1.27-1.67(m, 4H), 1.52(d, 1H), 1.81-1.87(m, 4H), 2.23(s, 3H), 2,96(s, 3H), 3.12(brs, 1H), 3.45(s, 3H), 4.32(s, 2H), 6.68(d, 1H), 7.19(d, 1H), 7.25(d, 1H), 7.68-7.71(m, 1H) |

TABLE 23

| Compd. No. | Form | ¹H-NMR (CDCl₃/TMS, δ (ppm)) |
|---|---|---|
| 138 | oil | 1.09-1.13(m, 1H), 1.27-1.54(m, 4H), 1.68(d, 1H), 1.81-1.87(m, 4H), 2.27(s, 3H), 2.96(s, 3H), 3.14(brs, 1H), 6.72(d, 1H), 7.25-7.38(m, 5H), 7.48-7.57(m, 3H) |
| 139 | oil | 0.26(s, 9H), 1.12-1.15(m, 1H), 1.21-1.36(m, 4H), 1.70(d, 1H), 1.81-1.88(m, 4H), 2.25(s, 3H), 3.15(brs, 1H), 6.68(d, 1H), 7.23(d, 1H), 7.29(s, 1H), 7.57(brs, 1H) |
| 140 | oil | 1.22(t, 6H), 2.27(s, 3H), 3.33-3.48(m, 4H), 6.71 (d, 1H), 7.25-7.34(m, 5H), 7.43(s, 1H), 7.49-7.51(m, 2H) |
| 141 | solid | 0.24 (s, 9H), 1.21(t, 6H), 2.18 (s, 3H), 2.35 (s, 3H), 3.38 (br, 4H), 6.54 (s, 1H), 7.21 (s, 1H), 7.39 (s, 1H) |
| 142 | oil | 0.93(t, 3H), 1.22(t, 3H), 1.63(brs, 2H), 2.26(s, 3H), 3.19-3.48(m, 4H), 6.70(d, 1H), 7.24-7.33(m, 5H), 7.42(s, 1H), 7.49-7.51(m, 2H) |
| 143 | oil | 0.95(t, 3H), 1.21(t, 3H), 1.36(brs, 2H), 1.58(brs, 2H), 2.26(s, 3H), 3.21-3.47(m, 4H), 6.69(d, 1H), 7.24-7.34(m, 5H), 7.42(brs, 1H), 7.48-7.51(m, 2H) |
| 144 | oil | 0.90(t, 3H), 1.22(t, 3H), 1.32(brs, 6H), 1.59(brs, 2H), 2.26(s, 3H), 3.22-3.47(m, 4H), 6.70(d, 1H), 7.26-7.35(m, 5H), 7.43(brs, 1H), 7.49-7.52(m, 2H) |
| 145 | oil | 1.55 (s, 6H), 1.60-1.80 (m, 6H), 2.19 (s, 3H), 2.35 (s, 3H), 3.44 (brs, 5H), 6.58 (s, 1H), 7.18 (s, 1H), 7.38 (s, 1H) |
| 146 | oil | 1.58-1.71(m, 6H), 2.26(s, 3H), 3.48(brs, 4H), 6.73(d, 1H), 7.26-7.34(m, 5H), 7.43(s, 1H), 7.50(d, 2H) |
| 147 | solid | 0.24 (s, 9H), 2.16 (s, 3H), 2.36 (s, 3H), 3.40-3.60 (m, 4H), 3.70-3.78 (m, 4H), 6.57 (s, 1H), 7.22 (s, 1H), 7.41 (s, 1H) |
| 148 | solid | 0.23 (s, 9H), 1.57-1.62 (m, 4H), 1.65-1.70 (m, 2H), 2.17 (s, 3H), 2.35 (s, 3H), 3.45 (brs, 4H), 6.56 (s, 1H), 7.21(s, 1H), 7.37 (s, 1H) |
| 149 | oil | 1.18-1.32 (m, 3H), 3.00-3.09 (m, 2H), 3.32 (s, 1H), 3.32-3.61 (m, 2H), 6.82-6.94 (m, 1H), 7.36-7.60 (m, 2H) |
| 150 | oil | 0.68 (q, 6H), 1.06 (t, 9H), 1.18-1.30 (m, 3H), 2.98-3.09 (m, 3H), 3.27-3.60 (m, 2H), 6.81-6.90 (m, 1H), 7.35-7.55 (m, 2H) |
| 151 | oil | 0,17 (s, 9H), 1.22-1.25 (m, 3H), 1.74 (s, 2H), 3.04 (s, 3H), 3.30-3.35 (m, 2H), 6.87 (s, 1H), 7.38 (s, 1H), 7.51 (s, 1H) |
| 152 | oil | 0.24 (s, 9H), 1.14-1.30 (m, 3H), 3.02 (s, 3H), 3.27-3.58 (m, 2H), 6.74-6.86 (m, 1H), 7.38-7.54 (m, 2H), 7.67 (s, 1H) |

TABLE 24

| Compd. No. | Form | ¹H-NMR (CDCl₃/TMS, δ (ppm)) |
|---|---|---|
| 153 | oil | 0.24 (s, 9H), 1.87-2.00 (m, 4H), 2.19 (s, 3H), 2.35 (s, 3H), 3.46-3.58 (m, 4H), 6.56 (s, 1H), 7.21 (s, 1H), 7.64 (s, 1H) |
| 154 | oil | 1.21 (t, 3H), 2.18 (s, 3H), 3.01 (s, 3H), 3.21 (s, 1H), 3.43 (brs, 2H), 6.48 (d, 1H), 7.21 (d, 1H), 7.39 (brs, 1H) |
| 155 | oil | 1.21 (t, 3H), 1.32 (s, 9H), 2.17 (s, 3H), 3.00 (s, 3H), 3.21-3.62 (m, 2H), 6.46 (d, 1H), 7.12 (d, 1H), 7.29-7.56 (m, 1H) |
| 156 | oil | 1.22 (t, 3H), 2.21 (s, 3H), 3.02 (s, 3H), 3.24-3.62 (m, 2H), 6.52 (d, 1H), 7.21-7.58 (m, 7H) |
| 157 | oil | 0.16 (s, 9H), 1.21 (t, 3H), 1.73 (s, 2H), 2.17 (s, 3H), 3.00 (s, 3H), 3.21-3.61 (m, 2H), 6.46 (d, 1H), 7.10 (d, 1H), 7.30-7.51 (m, 1H). |
| 158 | oil | 0.24 (s, 9H), 1.21 (t, 3H), 2.17 (s, 3H), 3.00 (s, 3H), 3.44 (brs, 2H), 6.46 (d, 1H), 7.19 (d, 1H), 7.40 (brs, 1H) |
| 159 | oil | 0.67 (q, 6H), 1.04 (t, 9H), 1.20 (t, 3H), 2.17 (s, 3H), 3.00 (s, 3H), 3.41 (brs, 2H), 6.46 (d, 1H), 7.19 (d, 1H), 7.36 (brs, 1H) |
| 160 | oil | 1.20 (t, 3H), 1.62 (s, 6H), 2.19 (s, 3H), 2.33 (s, 3H), 2.99 (s, 3H), 3.28-3.54 (m, 2H), 6.56 (s, 1H), 7.15 (s, 1H), 7.40 (brs, 1H) |
| 161 | oil | 0.22 (s, 9H), 1.20 (t, 3H), 1.58 (s, 6H), 2.20 (s, 3H), 2.34 (s, 3H), 2.99 (s, 3H), 3.20-3.66 (m, 2H), 6.56 (s, 1H), 7.15 (s, 1H), 7.42 (brs, 1H) |
| 162 | solid | 0.25 (s, 9H), 1.37 (s, 3H), 2.38 (s, 3H), 2.42 (s, 3H), 2,59 (brs, 1.5H), 3.34 (s, 0.7H), 3.58-3.63 (m, 3.5H), 4.08-4.13 (m, 0.5H), 7.14 (brs, 1H), 7.29 (m, 1H), 7.58-7.68 (m, 1H), 12.71-12.80 (m, 1H) |
| 163 | solid | 0.19 (s, 6H), 1.00 (s, 9H), 1.39 (brs, 3H), 2.39 (s, 3H), 2.43 (s, 3H), 3.34 (s, 1H), 3.56-4.21 (m, 4H), 7.13 (brs, 1H), 7.31 (s, 1H), 7.65 (br, 1H), 13.07 (br, 1H) |
| 164 | solid | 2.49 (s, 3H), 2.65 (s, 3H), 7.71 (s, 1H), 10.93 (s, 3H) |
| 165 | solid | 2.55 (s, 9H), 2,71 (s, 3H), 7.77 (s, 1H), 10.99 (s, 4H) |
| 166 | solid | 2.27 (s, 3H), 3.22 (s, 6H), 6.85 (s, 1H), 7.34-7.38 (m, 4H), 7.54-7.57 (m, 2H), 8.44 (s, 1H) |
| 167 | solid | 1.58-1.62 (m, 4H), 1.67-1.72 (m, 2H), 2.22 (s, 3H), 3.33-3,63 (brs, 4H), 6.83 (s, 1H), 7.20-7.26 (m, 2H), 7.36 (s, 1H), 7.39-7.43 (m, 2H), 7.57-7.59 (m, 1H) |

DMSO-d₆ was used as a solvent for the preparation of the measurement samples of compound Nos. 164 and 165.

TABLE 25

| Compd. No. | Form | $^1$H-NMR (CDCl$_3$/TMS, δ (ppm)) |
|---|---|---|
| 168 | oil | 1.21-1.28 (m, 3H), 2.23 (s, 3H), 3.01 (s, 1H), 3.31-3,51 (brs, 2H), 6.82 (s, 1H), 7.20-7.26 (m, 2H), 7.37-7.50 (m, 3H), 7.57-7.58 (m, 1H) |
| 169 | oil | 2.23 (s, 3H), 3.03 (s, 6H), 6.81(s, 1H), 7.20-7.25 (m, 2H), 7.40-7.44 (m, 3H), 7.56 (m, 1H) |
| 170 | solid | 0.26 (s, 9H), 1.35 (s, 3H), 2.22 (s, 3H), 2.31 (s, 6H), 3.31 (s, 0.7H), 3.49 (s, 2H), 3.60 (q, 1.5H), 3.92-3.94 (m, 0.5H), 7.01 (d, 3H), 7.21 (s, 1H), 7.58 (d, 1H), 11.8 (d, 1H): E/Z mixture |
| 171 | solid | 1.39 (s, 13H), 1.40-1.46 (m, 4H), 1.61 (s, 4H), 2.47 (s, 4H), 3.36 (s, 1H), 3.60-3.68 (m, 5H), 4,19-4.23 (m, 1H), 7.31 (s, 1.5H), 7.51 (d, 0.5H), 7.60 (d, 1H), 13.3-13.4 (m, 1H) |
| 172 | solid | 0.17 (s, 6H), 0.99 (s, 9H), 1.24 (d, 6H), 2.18 (s, 3H), 2.37 (s, 3H), 2.90 (brs, 3H), 3.64 (br, 1H), 6.56 (s, 1H), 7.22 (s, 1H), 7.50 (br, 1H): E/Z mixture |
| 173 | solid | 0.83 (s, 3.5H), 1.15 (s, 3.5H), 1.55-1.78 (m, 15H), 1.83-1.90 (m, 1H), 1.92 (s, 5H), 1.95 (s, 1H), 2.24 (d, 1H), 2.28 (s, 3H), 2.59 (t, 1H), 2.62 (d, 1H), 3.21 (d, 1H), 3.35 (s, 0.5H), 3.55 (s, 2.5H), 3.62-3.67 (m, 1.5H), 3.94-3.98 (m, 0.5H), 7.26-7.33 (m, 6H), 7.65 (s, 1H), 12.6 (brs, 1H): E/Z mixture |
| 174 | solid | 1.40 (s, 9H), 1.42 (s, 6H), 1.71-1.75 (m, 5H), 1.89-1.94 (m, 4H), 1.96-1.98 (m, 2H), 2.01-2.07 (m, 10H), 2.91 (d, 2H), 3.35 (d, 3H), 3.61 (s, 2H), 3.97 (s, 1H), 4.35 (brs, 4H), 7.09 (s, 1H), 7.30 (s, 3H), 7.54 (d, 1H), 11.7 (brs, 1H): E/Z mixture |
| 175 | solid | 0.38 (s, 9H), 0.88 (s, 3.H), 1.38 (s, 3H), 1.41 (s, 1H), 1.44 (t, 2.5H), 1.53 (s, 1H), 1.83-1.99 (m, 6H), 2.26-2.38 (m, 7H), 2.59-2,62 (m, 1H), 2.73 (d, 1H), 3.25 (d, 1H), 3.28 (d, 1H), 3.55-3.61 (m, 4H), 4.00-4.04 (m, 9.5H), 7.02 (s, 1H), 7.31 (s, 1H), 7.52 (d, 1H), 12.1 (d, 1H): E/Z mixture |
| 176 | solid | 1.33 (s, 9H), 1.38 (t, 3H), 2.43 (s, 3H), 3.38 (s, 1H), 3.58 (s, 2H), 3.65-4.12 (m, 2H), 7.12 (d, 1H), 7.24 (d, 1H), 7.88-7.99 (m, 1H), 12.79-12.91 (m, 1H) |
| 177 | solid | 1.31-1.45 (m, 3H), 2.48 (s, 3H), 3.40 (s, 1H), 3.59 (s, 2H), 3.65-4.14 (m, 2H), 7.20-7.39 (m, 5H), 7.48-7.57 (m, 2H), 7.93-8.10 (m, 1H), 12.70-12.89 (m, 1H) |
| 178 | solid | 0.69 (q, 6H), 1.05 (t, 9H), 1.40 (s, 3H), 3.44 (s, 1H), 3.60 (s, 2H), 3.70-4.16 (m, 2H), 7.55 (s, 1H), 7.87 (s, 1H), 8.23 (brs, 1H), 12.96 (br, 1H) |
| 179 | solid | 0.25 (s, 9H), 1.60 (brs, 6H), 1.80-1.87 (brs, 7H), 2.38 (s, 3H), 2.44 (s, 3H), 3.60 (brs, 2H), 4.40 (brs, 2H), 7.02 (brs, 1H), 7,43 (s, 1H), 7.52 (brs, 1H), 13.27 (brs, 1H) |
| 180 | solid | 2.55 (s, 3H), 3.38 (s, 3H), 3.65 (s, 3H), 7.21-7.25 (m, 4H), 7.29-7.31 (m, 1H), 7.35-7.37 (m, 2H), 7.43-7.45 (m, 1H), 7.72-7.74 (m, 1H), 7.76 (d, 1H), 13.0 (d, 1H): E/Z mixture |

The preparation method of the agricultural and horticultural fungicide of the present invention is described in detail below with reference to typical Formulation Examples.

Formulation Example 1

Emulsifiable Concentrate

Each of the compounds of the present invention (10 parts) was dissolved in 45 parts of Solvesso 150 and 35 parts of N-methylpyrrolidone, and 10 parts of an emulsifier (trade name: Sorpol 3005x, produced by Toho Chemical Industry Co., Ltd.) was added thereto, followed by stirring and mixing, thereby obtaining a 10% emulsifiable concentrate of each compound.

Formulation Example 2

Wettable Powder

Each of the compounds of the present invention (20 parts) was added to a mixture of 2 parts of sodium lauryl sulfate, 4 parts of sodium lignin sulfonate, 20 parts of synthetic water-containing silicon oxide powder, and 54 parts of clay, and stirred and mixed by a mixer, thereby obtaining a 20% wettable powder.

Formulation Example 3

Granules

Sodium dodecylbenzenesulfonate (2 parts), 10 parts of bentonite, and 83 parts of clay were added to 5 parts of each of the compounds of the present invention, and stirred and mixed sufficiently. An adequate amount of water was added, further stirred, granulated with a granulator, and forced-air dried, thereby obtaining 5% granules.

Formulation Example 4

Dust Formulation

Each of the compounds of the present invention (1 part) was dissolved in an adequate amount of acetone, and 5 parts of synthetic water-containing silicon oxide powder, 0.3 parts of PAP (acidic isopropyl phosphate), and 93.7 parts of clay were added thereto, followed by stirring and mixing by a juice mixer, and removal of acetone by evaporation, thereby obtaining a 1% dust formulation.

Formulation Example 5

Flowable

Each of the compounds of the present invention (20 parts) and 1.5 parts of sorbitan trioleate were mixed with 28.5 parts of an aqueous solution containing 2 parts of polyvinyl alcohol, and pulverized with a sand grinder (particle size: 3 microns or less). Then, 40 parts of an aqueous solution containing 0.05 parts of xanthan gum and 0.1 parts of aluminum magnesium silicate was added thereto, and 10 parts of propylene glycol was further added, followed by stirring and mixing, thereby obtaining a 20% water suspension.

Next, the availability of the compounds of the present invention as active ingredients of fungicides is demonstrated by Test Examples.

Test Example 1

Test of Preventive Effect on Cucumber Powdery Mildew

An aqueous solution of Sorpol 355 (produced by Toho Chemical Industry Co., Ltd.) (100 ppm) was added to an acetone solution of the compound of the present invention to prepare a test solution (the content of the compound of the present invention: 500 ppm). The test solution (4 ml) was sprayed to 1.2-leaf-stage cucumber seedlings (type: Suzunari Suyo) planted in a 7.5-cm-diameter pot using a spray gun. After air-drying, the seedlings were inoculated by spraying with a spore suspension of powdery mildew (*Sphaerotheca cucurbitae*). About ten days later, the degree of development of the disease was examined, and the preventive value was calculated by the following formula:

Preventive value=(1−(diseased area ratio in treated plot)/(diseased area ratio in untreated plot))×100

The results of the test on the compounds of the present invention represented by compound numbers 1, 2, 3, 4, 5, 13, 17, 25, 33, 34, 36, 37, 38, 42, 45, 46, 47, 49, 51, 52, 54, 56, 57, 61, 63, 64, 65, 66, 67, 68, 70, 72, 74, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 130, 132, 133, 134, 135, 136, 139, 140, 141, 142, 144, 145, 146, 147, 148, 149, 150, 151, 152, 153, 154, 155, 157, 158, 159, 160, 161, 162, 163, 167, 168, 169, 170, 171, 172, 173, 174, 175, 176, 178, 179, and 180 shown in Tables 5 to 13 above showed that all of the compounds had a preventive value of 50% or more.

Test Example 2

Test of Preventive Effect on Cucumber Gray Mold

An aqueous solution of Sorpol 355 (produced by Toho Chemical Industry Co., Ltd.) (100 ppm) was added to an acetone solution of the compound of the present invention to prepare a test solution (the content of the compound of the present invention: 500 ppm). The test solution (4 ml) was sprayed to 1.2-leaf-stage cucumber seedlings (type: Suzunari Suyo) planted in a 7.5-cm-diameter pot using a spray gun. After air-drying, the cotyledon of the cucumber seedlings was cut and placed in a plastic case lined with wet kitchen paper. Subsequently, 50 µl of a spore suspension of gray mold (*Botrytis cinerea*; $1 \times 10^6$ spores/ml) was added dropwise to the center of the cut cotyledon, and an 8-mm-diameter paper disc was placed thereon. Further, 50 µl of yeast-glucose liquid medium was added dropwise, and the resultant was allowed to stand in a thermostatic chamber (20±2° C., 24D, humid state). Four days after inoculation, the necrotic lesion diameter (mm) was measured, and the preventive value was calculated by the following formula:

Preventive value=(1−(average necrotic lesion diameter in treated plot)/(average necrotic lesion diameter in untreated plot))×100

The results of the test on the compounds of the present invention represented by compound numbers 2, 108, 110, 112, 114, and 117 shown in Tables 5 and 10 above showed that all of the compounds had a preventive value of 50% or more.

Test Example 3

Test of Preventive Effect on Rice Blast

An aqueous solution of Sorpol 355 (produced by Toho Chemical Industry Co., Ltd.) (100 ppm) was added to an acetone solution of the compound of the present invention to prepare a test solution (the content of the compound of the present invention: 500 ppm). The test solution (4 ml) was sprayed to 2-leaf-stage rice seedlings (type: Koshihikari) planted in a 7.5-cm-diameter pot using a spray gun. After air-drying, the seedlings were inoculated by spraying with a spore suspension of rice blast (*Pyricularia oryzae*; $4 \times 10^5$ spores/ml). The seedlings were placed in a constant-temperature, high-humidity chamber (25±1° C., 24D, humid state) for 24 hours, and then allowed to stand at 24° C. and at a humidity of 70% or more under fluorescence illumination. Seven days after inoculation, the degree of development of the disease was examined, and the preventive value was calculated by the following formula:

Preventive value=(1−(diseased area ratio in treated plot)/(diseased area ratio in untreated plot))×100

The results of the test on the compounds of the present invention represented by compound numbers 110 and 126 shown in Tables 10 and 11 above showed that all of the compounds had a preventive value of 50% or more.

Test Example 4

Test of Preventive Effect on Tomato Late Blight

An aqueous solution of Sorpol 355 (produced by Toho Chemical Industry Co., Ltd.) (100 ppm) was added to an acetone solution of the compound of the present invention to prepare a test solution (the content of the compound of the present invention: 500 ppm). The test solution (4 ml) was sprayed to 4.5-leaf-stage tomato seedlings (type: Minicarol) planted in a 7.5-cm-diameter pot using a spray gun. After air-drying, the seedlings were inoculated by spraying with a spore suspension of tomato late blight (*Phytophthora infestans*; $2 \times 10^5$ spores/ml). The seedlings were placed in a constant-temperature, high-humidity chamber (25±1° C., 24D, humid state) for 24 hours, and then allowed to stand in a thermostatic chamber at 20° C. and at a humidity of 70% or more. Five days after inoculation, the degree of development of the disease was examined, and the preventive value was calculated by the following formula:

Preventive value=(1−(diseased area ratio in treated plot)/(diseased area ratio in untreated plot))×100

The results of the test on the compounds of the present invention represented by compound numbers 13, 34, 36, 39, 64, 72, 78, 80, 104, 106, 107, 121, 124, 128, 146, and 152 shown in Tables 5, 6, 8, 10, 11, and 12 above showed that all of the compounds had a preventive value of 50% or more.

Test Example 5

Test of Preventive Effect on Wheat Powdery Mildew

An aqueous solution of Sorpol 355 (produced by Toho Chemical Industry Co., Ltd.) (100 ppm) was added to an acetone solution of the compound of the present invention to prepare a test solution (the content of the compound of the present invention: 500 ppm). The test solution (4 ml) was sprayed to 2-leaf-stage wheat seedlings (type: Shirasagi-komuqi) planted in a 7.5-cm-diameter pot using a spray gun. After air-drying, the seedlings were inoculated with wheat powdery mildew (Erysiphe graminis) conidiospore. The seedlings were allowed to stand in a thermostatic chamber (18° C., 12 hours, fluorescent lamp illumination). Seven days after inoculation, the degree of development of the disease was examined, and the preventive value was calculated by the following formula:

Preventive value=(1−(diseased area ratio in treated plot)/(diseased area ratio in untreated plot))×100

The results of the test on the compounds of the present invention represented by compound numbers 1, 2, 4, 5, 13, 17, 33, 37, 38, 42, 45, 46, 47, 49, 51, 52, 54, 56, 57, 60, 61, 62, 63, 64, 65, 67, 69, 70, 76, 77, 78, 79, 80, 81, 82, 83, 84, 85, 86, 88, 89, 91, 92, 93, 94, 95, 97, 98, 99, 100, 101, 102, 104, 105, 106, 107, 109, 110, 111, 112, 113, 114, 115, 116, 117, 118, 119, 120, 121, 122, 123, 124, 125, 126, 127, 128, 130, 132, 133, 134, 135, 136, 139, 140, 141, 142, 144, 145, 147, 148, 149, 150, 153, 158, 159, 160, 161, 162, 163, and 168 shown in Tables 5, 6, 7, 8, 9, 10, 11, 12, and 13 above showed that all of the compounds had a preventive value of 50% or more.

When the same test as in Test Example 5 was performed on the compound of number 129 (Reference Compound A) and the compound of number 8 (Reference Compound B) shown in Table 1 of Patent Document 11, both compounds showed a preventive value of 50% or more.

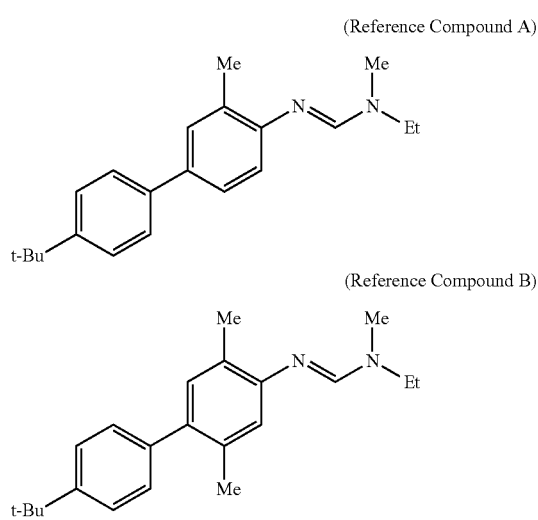

In addition, the same test was performed on the compound of the present invention represented by compound number 123 (Compound 123) and Reference Compounds A and B after the concentration of their test solutions was adjusted to a low level.

Table 26 shows the results.

TABLE 26

|  | Preventive value | | | |
| --- | --- | --- | --- | --- |
| Treatment concentration | 100 ppm | 40 ppm | 20 ppm | 10 ppm |
| Compound 123 | 100 | 100 | 100 | 100 |
| Reference Compound A | 100 | 70 | 20 | 10 |
| Reference Compound B | 95 | 70 | 70 | 40 |

Table 26 demonstrates that the compound of the present invention (Compound 123) showed excellent control performance even at a low concentration, while the control performance of the Reference Compounds A and B was decreased as the concentration decreased.

Test Example 6

Test of Inhibition of Growth of Wheat Scab Mycelium

Wheat scab (Microdochium nivale) strains were cultured in a potato-dextrose agar (PDA) flat medium at 25° C. The PDA medium was dissolved in an autoclave (110° C., 3 minutes), dispensed into test tubes in 15 ml quantities, and subjected to high-pressure sterilization in an autoclave (120° C., 15 minutes). The test tube containing the medium was cooled to 50° C., and the compound of the present invention was added so that the final concentration was 10 ppm. The resulting mixture was poured into a petri dish (a shallow Nissui P dish). After solidification of the medium, a 5-mm-diameter mycelial disk was implanted from the tip of bacterial flora grown in the above-mentioned petri dish, and cultured at 25° C. for 2 to 3 days. Thereafter, the growth length of the mycelium was measured, and the inhibition rate was calculated in comparison with the untreated sample.

The results of the test on the compounds of the present invention represented by compound numbers 2, 3, 4, 12, 25, 29, 34, 41, 42, 47, 52, 54, 55, 59, 66, 67, 68, 69, 70, 76, 86, 91, 93, 94, 96, 97, 98, 99, 100, 101, 102, 104, 105, 106, 107, 108, 109, 110, 111, 112, 113, 114, 115, 116, 117, 118, 119, 120, 121, 123, 124, 126, 127, 128, 132, 134, 141, 145, 147, 151, 153, 155, 156, 157, 158, 162, 163, 170, 171, 172, 173, 174, 175, 176, 177, and 179 shown in Tables 5, 6, 7, 8, 9, 10, 11, 12, and 13 above showed that all of the compounds had an inhibition rate of 100%.

Test Example 7

Test of Effect on Cucumber Powdery Mildew (Vaporization Properties)

A 10-mm square piece of aluminum foil was attached with a double-sided tape on the first leaf of cucumber planted in a 7.5-cm-diameter pot. Then, an aqueous solution of Sorpol 355 (produced by Toho Chemical Industry Co., Ltd.) was added to an acetone solution of the compound of the present invention to prepare a 100 ppm drug solution (the content of the compound of the present invention: 100 ppm). The drug solution was added dropwise in 50-µ amounts using a micropipette. After air-drying the drug solution, the leaf was inoculated by spraying with a spore suspension of powdery mildew (Sphaerotheca cucurbitae). Seven days after inoculation, the diameter of a disease development inhibition circle on the cucumber first leaf was measured. The appearance of necrotic lesions on the leaf was examined in comparison with

TABLE 27

| Test compound | Diameter of disease development inhibition circle (cm) |
|---|---|
| Compound 69 | 2.75 |
| Compound 85 | 6.0 |
| Compound 91 | 6.0 |
| Compound 93 | 6.0 |
| Compound 98 | 9.5 |
| Compound 123 | 9.5 |
| Compound 124 | 3.75 |
| Compound 126 | 6.5 |
| Compound 127 | 2.0 |
| Compound 147 | 2.5 |
| Compound 158 | 3.75 |
| Compound 161 | 6.0 |
| Compound 162 | 8.0 |
| Compound 163 | 8.0 |
| Compound 170 | 9.5 |
| Compound 171 | 7.0 |
| Compound 172 | 7.0 |
| Compound 174 | 7.0 |
| Compound 175 | 7.0 |
| Compound 176 | 7.0 |
| Reference Compound A | 0 |
| Reference Compound B | 0 |

The invention claimed is:

1. An ethynylaniline compound represented by Formula (4):

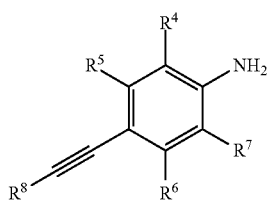

(4)

wherein $R^4$ and $R^6$ are each halogen or $C_{1-4}$ alkyl;
$R^5$ and $R^7$ are each hydrogen; and
$R^8$ is hydrogen; $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —(CH$_2$)n-Si(R$^9$)(R$^{10}$)(R$^{11}$) wherein R$^9$, R$^{10}$, and R$^{11}$ are each $C_{1-6}$ alkyl, and n is an integer of 0 or 1.

2. The ethynylaniline compound according to claim 1, wherein $R^8$ is $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{3-8}$ cycloalkyl; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —(CH$_2$)n-Si(R$^9$)(R$^{10}$)(R$^{11}$) wherein R$^9$, R$^{10}$, and R$^{11}$ are each $C_{1-6}$ alkyl, and n is an integer of 0 or 1.

3. The ethynylaniline compound according to claim 2, wherein $R^8$ is $C_{1-20}$ alkyl optionally substituted on the alkyl group with one or more substituents independently selected from the group consisting of $C_{1-4}$ alkoxy, hydroxy, cyano, phenyl, phenoxy, and optionally substituted heterocyclic groups; $C_{1-4}$ haloalkyl; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —(CH$_2$)n-Si(R$^9$)(R$^{10}$)(R$^{11}$) wherein R$^9$, R$^{10}$, and R$^{11}$ are each $C_{1-6}$ alkyl, and n is an integer of 0 or 1.

4. The ethynylaniline compound according to claim 3, wherein $R^8$ is $C_{1-20}$ alkyl optionally substituted on the alkyl group with one or more substituents independently selected from the group consisting of cyano, phenyl, and optionally substituted heterocyclic groups; phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —(CH$_2$)n-Si(R$^9$)(R$^{10}$)(R$^{11}$) wherein R$^9$, R$^{10}$, and R$^{11}$ are each $C_{1-6}$ alkyl, and n is an integer of 0 or 1.

5. The ethynylaniline compound according to claim 4, wherein $R^8$ is phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; a heterocyclic group optionally substituted on the heterocyclic ring with one or more substituents independently selected from the group consisting of halogen, $C_{1-4}$ alkyl, $C_{1-4}$ haloalkyl, and optionally substituted heterocyclic groups; or —(CH$_2$)n-Si(R$^9$)(R$^{10}$)(R$^{11}$) wherein R$^9$, R$^{10}$, and R$^{11}$ are each $C_{1-6}$ alkyl, and n is an integer of 0 or 1.

6. The ethynylaniline compound according to claim 5, wherein $R^8$ is phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy; or —(CH$_2$)n-Si(R$^9$)(R$^{10}$)(R$^{11}$) wherein R$^9$, R$^{10}$, and R$^{11}$ are each $C_{1-6}$ alkyl, and n is an integer of 0 or 1.

7. The ethynylaniline compound according to claim 6, wherein $R^8$ is phenyl optionally substituted on the phenyl ring with one to five substituents independently selected from the group consisting of halogen, $C_{1-6}$ alkyl, $C_{1-4}$ haloalkyl, $C_{1-4}$ alkoxy, and phenoxy.

8. The ethynylaniline compound according to claim 6, wherein the ethynylaniline compound is represented by Formula (4) wherein $R^8$ is —$(CH_2)$n-Si$(R^9)(R^{10})(R^{11})$ wherein $R^9$, $R^{10}$, and $R^{11}$ are each $C_{1-6}$ alkyl, and n is an integer of 0 or 1.

9. The ethynylaniline compound according to claim 7, wherein $R^4$ and $R^6$ are each fluorine, chlorine, or methyl.

10. The ethynylaniline compound according to claim 9, wherein $R^4$ and $R^6$ are each methyl.

11. The ethynylaniline compound according to claim 8, wherein the ethynylaniline compound is represented by Formula (4) wherein $R^4$ and $R^6$ are each fluorine, chlorine, or methyl.

12. The ethynylaniline compound according to claim 11, wherein the ethynylaniline compound is represented by Formula (4) wherein $R^4$ and $R^6$ are each methyl.

13. The ethynylaniline compound according to claim 1, wherein the ethynylaniline compound is represented by Formula (4) wherein $R^4$ and $R^6$ are each halogen or $C_{1-4}$ alkyl.

14. The ethynylaniline compound according to claim 13, wherein the ethynylaniline compound is represented by Formula (4) wherein $R^4$ and $R^6$ are each fluorine, chlorine, or methyl.

15. The ethynylaniline compound according to claim 14, wherein the ethynylaniline compound is represented by Formula (4) wherein $R^4$ and $R^6$ are each methyl.

* * * * *